(12) United States Patent
Sohn et al.

(10) Patent No.: US 8,778,626 B2
(45) Date of Patent: Jul. 15, 2014

(54) CLICKABLE CROSS-LINKER

(75) Inventors: Chang Ho Sohn, Pasadena, CA (US); Jesse L. Beauchamp, La Canada Flintridge, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/135,543

(22) Filed: Jul. 8, 2011

(65) Prior Publication Data

US 2012/0028285 A1 Feb. 2, 2012

Related U.S. Application Data

(60) Provisional application No. 61/362,652, filed on Jul. 8, 2010.

(51) Int. Cl.
*C12Q 1/37* (2006.01)
*C12P 21/06* (2006.01)
*C07D 403/12* (2006.01)

(52) U.S. Cl.
USPC .............. 435/23; 435/68.1; 436/89; 548/255; 548/520; 527/201

(58) Field of Classification Search
USPC ........ 435/23, 29, 68.1; 436/89; 548/520, 255; 527/201
See application file for complete search history.

(56) References Cited

U.S. PATENT DOCUMENTS

| | | | |
|---|---|---|---|
| 2006/0094121 A1 | 5/2006 | Reid et al. | |
| 2007/0140967 A1 | 6/2007 | Wood et al. | |
| 2009/0130769 A1 | 5/2009 | de Jong et al. | |

OTHER PUBLICATIONS

International Search Report and Written Opinion dated Feb. 20, 2012 for International Application No. PCT/ US2011/043472 (9 sheets).
Chowdhury, et al., "*Identification of Cross-Linked Peptides after Click-Based Enrichment Using Sequential Collision-Induced Dissociation and Electron Transfer Dissociation Tandem Mass Spectrometry*", Analytical Chemistry, vol. 81, No. 13, Jul. 1, 2009, pp. 5524-5532.
Leitner, et al., "*Probing Native Protein Structures by Chemical Cross-linking, Mass Spectrometry, and Bioinformatics*", Molecular & Cellular Proteomics; vol. 9, Mar. 31, 2012, pp. 1634-1649.
Tang, et al., "*Mass Spectrometry Identifiable Cross-Linking Strategy for Studying Protein-Protein Interactions*", Analytical Chemistry, vol. 77, No. 1, Jan. 1, 2005, pp. 311-318.
Back et al., *J. Mol. Biol.* 2003, 331, 303.
Back, J. W. et al., *Am. Soc. Mass Spectrom,* 2001, 12, 222.
Baskin, Jeremy M. et al.; "Copper-free click chemistry for dynamic in vivo imaging"; *Proc. Natl. Acad. Sci.,* Oct. 23, 2007, vol. 104, No. 43; pp. 16793-16797.
Brittain et al., *Nat. Biotechnol.* 2005, 23, 463.
Chu et al., *J. Am. Chem. Soc.* 2006, 128, 10362.
Collins et al., *Curr. Opin. Biotechnol.* 2008, 19, 324.
Collins et al., *Bioorg. Med. Chem. Lett.* 2003, 13, 4023.
Cronan, Jr., John E.; "Biotination of Proteins in Vivo: A Post-Translational Modification to Label, Purify, and Study Proteins"; *J. Biol. Chem.,* Jun. 25, 1990, vol. 265, No. 18; pp. 10327-10333.
Deshaies, R. J., *Annu. Rev. Cell Dev. Biol.* 1999, 15, 435.
Gardner et al., *Anal. Chem.* 2008, 80, 4807.
Gingras et al., *Nat. Rev. Mol. Cell Biol.* 2007, 8, 645.
Greenfield, N. J., *Nat. Protocols* 2007,1, 2876.
Guerrero et al., *Proc. Natl. Acad. Sci. U. S. A.* 2008, 105, 13333.
Hartwell, Leland H. et al.; "From molecular to modular cell biology"; *Nature;* Dec. 2, 1999, vol. 402, pp. C47-052.
Jenson et al., *Biochim. Biophys. Acta* 1980, 624, 378.
Jewett et al., *Chem. Soc. Rev.,* 2010, 39, 1272.
Kang et al., *Rapid Commun. Mass Spectrom.* 2009, 23, 1719.
King, R. W., et al., *Science* 1996, 274, 1652.
Kruppa et al., *Rapid Commun. Mass Spectrom.* 2003, 17, 155.
Kulman et al., *Protein Expr. Purif.* 2007, 52, 320.
Lauber, M. A.; Reilly, J. P. *Anal. Chem.* 2010, 82, 7736.
Lee, J. Eugene et al.; "The Steady-State Repertoire of Human SCF Ubiquitin Ligase Complexes Does Not Require Ongoing Nedd8 Conjugation"; *Mol. Cell. Proteomics,* Dec. 17, 2010, Electronic preprint. doi:10.1074/mcp.M110.006460; 10.5, 9 pp.
Lee, Y., *J. Mol. BioSyst.* 2008, 4, 816.
Muller et al., *Anal. Chem.* 2001, 73, 1927.
Nam et al., *Biomaterials* 2003, 24, 2053.
Nessen et al., *J. Proteome Res.* 2009, 8, 3702.
Nilsson et al., *J. Am. Chem. Soc.* 2008, 130, 11297.
Novak et al., *Eur. J. Mass Spectrom.* 2003, 9, 623.
Pereira-Leal, Jose B. et al.; "The origins and evolution of functional modules: lessons from protein complexes"; *Philosophical Transactions of the Royal Society B: Biological Sciences,* Feb. 3, 2006, 361, pp. 507-517.
Petrotchenko et al., *Mass Spectrom. Rev.* 2010, 29, 862.
Petrotchenko, Evgenly V. et al.; "Isotopically Coded Cleavable Cross-linker for Studying Protein-Protein Interaction and Protein Complexes"; *Mol. Cell. Proteomics* 4.8, 2005, pp. 1167-1179.
Pettersen et al., *Comput. Chem.* 2004, 25, 1605.
Rinner et al. *Nat. Methods* 2008, 5, 315.
Rostovtsev et al., *Angew. Chem.-Int. Edit.* 2002, 41, 2596.
Rozkiewicz et al., *Angew. Chem.-Int. Edit.* 2006, 45, 5292.
Saxon et al., *Science* 2000, 287, 2007.
Sharan, Roded et al.; "Conserved patterns of protein interaction in multiple species"; *Proc. Natl. Acad. Sci. U. S. A.,* Feb. 8, 2005, vol. 102, No. 6, pp. 1974-1979.
Sinz and Wang, *Anal. Biochem.* 2004, 331, 27.
Sinz et al., *Biochemistry* 2001, 40, 7903.
Sinz, A., *Anal. Bioanal. Chem.* 2010, 397, 3433.

(Continued)

*Primary Examiner* — Chih-Min Kam
(74) *Attorney, Agent, or Firm* — Christie, Parker & Hale, LLP.

(57) ABSTRACT

A clickable cross-linker compound provides an easily scanned reporter ion for effective and efficient cross-linking and identification of intermolecular and intramolecular interactions of proteins and peptides.

33 Claims, 11 Drawing Sheets
(3 of 11 Drawing Sheet(s) Filed in Color)

(56) References Cited

OTHER PUBLICATIONS

Sinz, A., *J. Mass Spectrom.* 2003, 38, 1225.
Sinz, A., *Mass Spectrom. Rev.* 2006, 25, 663.
Sohn et al., *J. Am. Chem. Soc.* 2009, 131, 5444.
Szychowski et al., *J. Am. Chem. Soc.* 2010, 132, 18351.
Tagwerker, Christian et al.; "A Tandem Affinity Tag for Two-step Purification under Fully Denaturing Conditions: Application In Ubiquitin Profiling And Protein Complex Identification Combined With In Vivo Cross-Linking"; *Mol. Cell. Proteomics,* Jan. 23, 2006, 5.3, pp. 737-748.
The Molecular Probes® Handbook, 11th Edition, Cross-linking and Photoactivatable Reagents, Chapter 5, Section 5.1 *Invitrogen Life Science;* Bioconjugate Reagents, Bioconjugate Techniques, Part I and II, 2nd Edition, by Greg T. Hermanson, Published by Academic Press, Inc., 2008.
The Molecular Probes® Handbook, 11th Edition, Cross-linking and Photoactivatable Reagents, *Photoreactive Crosslinking and Labeling Reagents,* Crosslinking and Photoreactive Reagents, Chapter 5, Section 5.3, Molecular Biotechnology (MoBiTech), by Greg T. Hermanson, Published by Academic Press, Inc., 2008.
Tornoe et al., *J. Org. Chem.* 2002, 67, 3057.
Trester-Zedlitz et al., *J. Am. Chem. Soc.* 2003, 125, 2416.
Trnka, Michael J. et al.; "Topographic Studies of the GroEL-GroES Chaperonin Complex by Chemical Cross-linking Using Diformyl Ethynylbenzene"; *Mol. Cell. Proteomics* 9.10, 2010, pp. 2306-2317.
Vellucci et al., *J. Am. Soc. Mass Spectrom.* 2010, 21, 1432.
Wine et al., *Anal. Chem.* 2002, 74, 1939.
Wong, S. S. *Chemistry of Protein Conjugation and Cross-Linking;* CRC Press, 1991; Phizicky and Fields, Rev. 1995, 59, 94.
Zhang, Haizhen et al.; "Identification of Protein-Protein Interactions and Topologies in Living Cells with Chemical Cross-linking and Mass Spectrometry"; *Mol. Cell. Proteomics* 2009, 8.3, pp. 409-420.
Back, Jaap Willem et al.; "Chemical Cross-linking and Mass Spectrometry for Protein Structural Modeling"; *J. Mol. Biol.;* 2003; 331; pp. 303-313.
Back, J. W. et al.; "A New Crosslinker for Mass Spectrometric Analysis of the Quaternary Structure of Protein Complexes"; *J. Am. Soc. Mass Spectrom;* 2001; 12; pp. 222-227.
Brittain, Scott M. et al.; "Enrichment and analysis of peptide subsets using fluorous affinity tags and mass spectrometry"; *Nat. Biotechnol.;* vol. 23; No. 4; Apr. 2005; pp. 463-468.
Chu, Feixia et al.; "Isotope-Coded and Affinity-Tagged Cross-Linking (ICATXL): An Efficient Strategy to Probe Protein Interaction Surfaces"; *J. Am. Chem. Soc.;* 2006; 128, pp. 10362-10363.
Collins, Mark O. et al.; "Mapping multiprotein complexes by affinity purification and mass spectrometry"; *Curr. Opin. Biotechnol.;* 2008; 19; pp. 324-330.
Collins, Christopher J. et al.; "Isotopically Labeled Crosslinking Reagents: Resolution of Mass Degeneracy in the Identification of Crosslinked Peptides"; *Bioorg. & Med. Chem. Lett.;* 2003; 13; pp. 4023-4026.
Deshaies, R. J.; "SCF and Cullin/RING H2-Based Ubiquitin Ligases"; *Annu. Rev. Cell Dev. Biol.;* 1999; 15; pp. 435-467.
Gardner, Myles W. et al.; "Chromogenic Cross-Linker for the Characterization of Protein Structure by Infrared Multiphoton Dissociation Mass Spectrometry"; *Anal. Chem.;* 2008; 80; pp. 4807-4819.
Gingras, Anne-Claude et al.; "Analysis of protein complexes using mass spectrometry"; *Nat. Rev.; Mol. Cell Biol.;* vol. 8; Aug. 2007; pp. 645-654.
Greenfield, Norma. J.; "Using circular dichroism spectra to estimate protein secondary structure"; *Nat. Protocols;* 2006, vol. 1; No. 6; pp. 2876-2890.
Guerrero, Cortnie et al.; "Characterization of the Proteasome Interaction Network Using a QTAX-Based Tag-Team Strategy and Protein Interaction Network Analysis"; *Proc. Natl. Acad. Sci.;* Sep. 9, 2008; vol. 105; No. 36; pp. 13333-13338.
Jenson, James et al.; "Physical-Chemical Properties of Ubiquitin"; *Biochim. et Biophys. Acta;* 1980; 624; pp. 378-385.
Jewett, John C. et al.; "Cu-free click cycloaddition reactions in chemical biology"; *Chem. Soc. Rev.;* 2010; 39; pp. 1272-1279.
Kang, Sebyung et al.; "Synthesis of biotin-tagged chemical cross-linkers and their applications for mass spectrometry"; *Rapid Commun. In Mass Spectrom.;* 2009; 23; pp. 1719-1726.
King, Randall. W. et al.; "How Proteolysis Drives the Cell Cycle"; *Science;* Dec. 6, 1996; vol. 274; No. 5293; pp. 1652-1659.
Kruppa, Gary H. et al.; "A top down approach to protein structural studies using chemical cross-linking and Fourier transform mass spectrometry"; *Rapid Commun. in Mass Spectrom.;* 2003; 17; pp. 155-162.
Kulman, John D. et al.; "A versatile system for site-specific enzymatic biotinylation and regulated expression of proteins in cultured mammalian cells"; *Protein Expr. & Purif.;* 2007; 52; pp. 320-328.
Lauber, Matthew A. et al.; "Novel Amidinating Cross-Linker for Facilitating Analyses of Protein Structures and Interactions"; *Anal. Chem.;* 2010; 82; pp. 7736-7743.
Lee, Young Jin; "Mass spectrometric analysis of cross-linking sites for the structure of proteins and protein complexes"; *Mol. BioSyst.;* 2008; 4, pp. 816-823.
Muller, D.R. et al.; "Isotope-Tagged Cross-Linking Reagents. A New Tool in Mass Spectrometric Protein Interaction Analysis"; *Anal. Chem.;* 2001; 73; pp. 1927-1934.
Nam, Yoon Sung et al.; "New micelle-like polymer aggregates made from PEI-PLGA diblock copolymers: micellar characteristics and cellular uptake"; *Biomaterials;* 2003; 24; pp. 2053-2059.
Nessen, Merel A. et al.; "Selective Enrichment of Azide-Containing Peptides from Complex Mixtures"; *J. of Proteome Res.;* 2009; 8; pp. 3702-3711.
Nilsson, Bradley L. et al.; "Enantioselective Total Syntheses of Nankakurines A and B: Confirmation of Structure and Establishment of Absolute Configuration"; *J. Am. Chem. Soc.;* 2008; 130; pp. 11297-11299.
Novak, Petr et al.; "A top-down approach to protein structure studies using chemical cross-linking and Fourier transform mass spectrometry"; *Eur. J. Mass Spectrom;* 2003; 9; pp. 623-631.
Petrotchenko, Evgeniy V. et al.; "Crosslinking Combined With Mass Spectrometry for Structural Proteomics"; *Mass Spectrom. Rev.;* 2010; 29; pp. 862-876.
Pettersen, Eric. F. et al.; "UCSF Chimera—A Visualization System for Exploratory Research and Analysis"; *Journal of Comput. Chem.;* 2004; vol. 25; No. 13; pp. 1605-1612.
Rinner, Oliver et al.; "Identification of crosslinked peptides from large sequence databases"; *Nat. Methods;* Apr. 2008; vol. 5; No. 4; pp. 315-318.
Rostovtsev, Vsevolod V. et al.; "A Stepwise Huisgen Cycloaddition Process: Copper$^{(l)}$-Catalyzed Regioselective "Ligation" of Azides and Terminal Alkynes"; *Angew. Chem. Int. Ed.;* 2002; 41; No. 14; pp. 2596-2599.
Rozkiewicz, Dorota I. et al.; ""Click" Chemistry by Microcontact Printing"; *Angew. Chem. Int. Ed.;* 2006; 45; pp. 5292-5296.
Saxon, Eliana et al.; "Cell Surface Engineering by a Modified Staudinger Reaction"; *Science;* Mar. 17, 2000; vol. 287; pp. 2007-2010.
Sinz, Andrea et al.; "Mapping spatial proximities of sulfhydryl groups in proteins using a fluorogenic cross-linker and mass spectrometry"; *Anal. Biochem.;* 2004, 331, pp. 27-32.
Sinz, Andrea et al.; "Mapping Protein Interfaces with a Fluorogenic Cross-Linker and Mass Spectrometry: Application to Nebulin-Calmodulin Complexes"; *Biochemistry;* 2001; 40; pp. 7903-7913.
Sinz, Andrea; "Investigation of protein-protein interactions in living cells by chemical crosslinking and mass spectrometry"; *Anal. Bioanal. Chem.;* 2010; 397; pp. 3433-3440.
Sinz, Andrea; "Chemical cross-linking and mass spectrometry for mapping three-dimensional structures of proteins and protein complexes"; *Journal of Mass Spectrometry;* 2003; 38; pp. 1225-1237.
Sinz, Andrea; "Chemical Cross-Linking and Mass Spectrometry to Map Three-Dimensional Protein Structures and Protein-Protein Interactions"; *Mass Spectrom. Rev.;* 2006; 25; pp. 663-682.
Sohn, Chang Ho et al.; "Probing the Mechanism of Electron Capture and Electron Transfer Dissociation Using Tags with Variable Electron Affinity"; *J. Am. Chem. Soc.;* 2009 131, pp. 5444-5459.
Szychowski, Janek et al.; "Cleavable Biotin Probes for Labeling of Biomolecules via Azide-Alkyne Cycloaddition"; *J. Am. Chem. Soc.;* 2010, 132, pp. 18351-18360.

(56) References Cited

OTHER PUBLICATIONS

The Molecular Probes® Handbook, 11th Edition, Cross-linking and Photoactivatable Reagents; *"Introduction to Crosslinking Photoactivatable Reagents";* Chapter 5, Section 5.1 Molecular Biotechnology (MoBiTech), by Greg T. Hermanson, Published by Academic Press, Inc., 2008; 4pp.

The Molecular Probes® Handbook; 11th Edition; Cross-linking and Photoactivatable Reagents; *"Photoreactive Reagents, Including Photoreactive Crosslinkers and Caged Probes";,* Chapter 5, Section 5.3, Molecular Biotechnology (MoBiTech), by Greg T. Hermanson, Published by Academic Press, Inc., 2008; 11pp.

Tornoe, Christian W et al.; "Peptidotriazoles on Solid Phase: [1,2,3]-Triazoles by Regiospecific Copper(I)-Catalyzed 1,3-Dipolar Cycloadditions of Terminal Alkynes to Azides"; *J. Org. Chem.;* 2002, 67, pp. 3057-3064.

Trester-Zedlitz, Michelle et al.; "A Modular Cross-Linking Approach for Exploring Protein Interactions"; *J. Am. Chem. Soc.;* 2003; 125; pp. 2416-2425.

Vellucci, Danielle et al.; "Selective Enrichment and Identification of Azide-tagged Cross-Linked Peptides Using Chemical Ligation and Mass Spectrometry"; *J. Am. Soc. Mass Spectrom.;* 2010, 21, pp. 1432-1445.

Wine, Robert N. et al.; "Identification of Components of Protein Complexes Using a Fluorescent Photo-Cross-Linker and Mass Spectrometry"; *Anal. Chem.;* 2002; 74; pp. 1939-1945.

Phizicky, Eric M. et al.; "Protein-protein interactions: methods for detection and analysis"; Microbiology and Molecular Biology Reviews; 1995; 59(1); pp. 94-123 (31pp).

Wong, S. S. Chemistry of Protein Conjugation and Cross-Linking; CRC Press, 1991.

FIG. 6

Table 1. Mono- and loop-linked peptides from ubiquitin.

| | Sequence | Before Click | After Click & SCX Fractionation | Reporter Ion |
|---|---|---|---|---|
| (SEQ ID NO: 7) | $^1$MQIFV$^6$K^TLTG$^{11}$K | Yes, 2+, 3+ | Yes, 2+, 3+, 250 mM | Yes |
| (SEQ ID NO: 4) | $^7$TLTG$^{11}$K^TITLEVEPSDTIENV$^{27}$K | Yes, 2+, 3+, 4+ | Yes, 3+, 4+, 250 mM | Yes |
| (SEQ ID NO: 8) | $^{12}$TITLEVEPSDTIENV$^{27}$K^A$^{29}$K | Yes, 3+ | Yes, 3+, 250 mM | Yes |
| (SEQ ID NO: 6) | $^{28}$A$^{29}$K^IQD$^{33}$K | Yes, 2+ | No | N/A |
| (SEQ ID NO: 9) | $^{28}$A$^{29}$K^IQDKEGIPPDQQ$^{42}$R | Yes, 3+ | No | N/A |
| (SEQ ID NO: 9) | $^{28}$AKIQD$^{33}$K^EGIPPDQQ$^{42}$R | Yes, 3+ | Yes, 4+, 250 mM | Yes |
| (SEQ ID NO: 3) | $^{30}$IQD$^{33}$K^EGIPPDQQ$^{42}$R | Yes, 2+, 3+ | Yes, 2+, 3+, 250 mM | Yes |
| (SEQ ID NO: 5) | $^{43}$LIFAG$^{48}$K^QLEDG$^{54}$R | Yes, 2+, 3+ | Yes, 2+, 3+, 4+, 50, 250 mM | Yes |
| (SEQ ID NO: 10) | $^{43}$LIFAG$^{48}$K^QLEDGRTLSDYNIQ$^{63}$K | Yes, 2+, 3+, 4+ | Yes, 3+, 4+, 250 mM | Yes |
| (SEQ ID NO: 11) | $^{55}$TLSDYNIQ$^{63}$K^ESTLHLVL$^{72}$R | Yes, 2+, 3+ | Yes, 3+, 4+, 250 mM | Yes |
| (SEQ ID NO: 7) | $^1$MQIFV$^6$K^TLTG$^{11}$K^ | Yes, 2+, 3+ | Yes, 2+, 3+, 250 mM | Yes |
| (SEQ ID NO: 9) | $^{28}$A$^{29}$K^IQD$^{33}$K^EGIPPDQQ$^{42}$R | Yes, 2+, 3+ | Yes, 3+, 250 mM | Yes |

^: linked residues. Superscript numbers are the residue numbers of amino acids of ubiquitin.

FIG. 7

Table 2. Cross-linked peptides from ubiquitin.

| α chain | β chain | Before Click | After Click & SCX Fractionation | Reporter Ion | Avidin Enrichment | Cα distance (Å) | NZ distance (Å) |
|---|---|---|---|---|---|---|---|
| ⁶³LIFAG⁶⁸K*QLEDG⁷⁵R (SEQ ID NO: 5) | ¹MQIFV⁶K*TLTG¹¹K (SEQ ID NO: 7) | Yes, 3+, 4+, 5+ | No | N/A | No | 15.14 | 17.82 |
| ¹MQIFV⁶K*TLTG¹¹K (SEQ ID NO: 7) | ⁷TLSDYNIQ¹⁵K*ESTLHLVL²⁷R (SEQ ID NO: 11) | Yes, 5+, 6+ | No | N/A | No | 15.01 | 20.31 |
| ³⁰IQD³³K*EGIPPDQQ⁴²R (SEQ ID NO: 3) | ⁷TLTG¹¹K*TITLEVEPSDTIENV⁶K (SEQ ID NO: 4) | Yes, 4+, 5+ | Yes, 4+, 5+, 250 mM, 1st 500 mM, 2nd 500 mM | Yes | Yes, 4+, 5+ | 12.85 | 7.15 |
| ⁶³LIFAG⁶⁸K*QLEDG⁷⁵R (SEQ ID NO: 5) | ⁶³LIFAG⁶⁸K*QLEDG⁷⁵R (SEQ ID NO: 5) | Yes, 3+, 4+, 5+ | Yes, 5+, 2nd 500 mM | Yes | Yes, 5+ | N/A | N/A |
| ⁶³LIFAG⁶⁸K*QLEDG⁷⁵R (SEQ ID NO: 5) | ⁷TLSDYNIQ¹⁵K*ESTLHLVL²⁷R (SEQ ID NO: 11) | Yes, 6+ | No | N/A | No | 17.89 | 19.83 |
| ²⁸A²⁹K*IQD³³K (SEQ ID NO: 6) | ³⁰IQD³³K*EGIPPDQQ⁴²R (SEQ ID NO: 3) | No | No | Yes | Yes, 5+ | 6.24 | 9.09 |

*: cross-linked residues. Superscript numbers are the residue numbers of amino acids of ubiquitin.

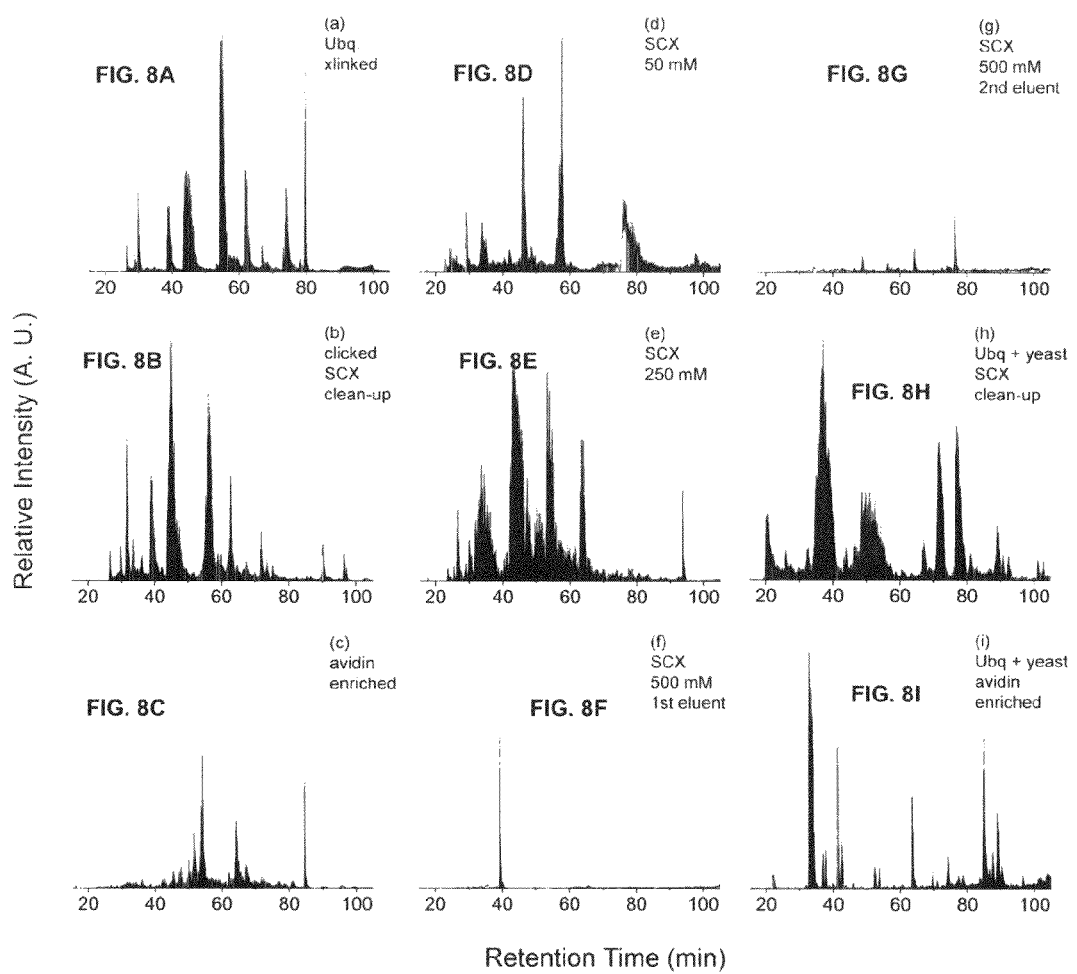

```
                        SEQUENCE LISTING

<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: model peptide

<400> SEQUENCE: 1

Ala Ala Lys Ala Ala Ala Ala Ala Lys Ala Arg
1               5                   10

<210> SEQ ID NO 2
<211> LENGTH: 11
<212> TYPE: PRT
<213> ORGANISM: artificial sequence
<220> FEATURE:
<223> OTHER INFORMATION: model peptide

<400> SEQUENCE: 2

Ala Ala Ala Ala Lys Ala Ala Ala Ala Ala Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: ubiquitin cross-linked peptide

<400> SEQUENCE: 3

Ile Gln Asp Lys Glu Gly Ile Pro Pro Asp Gln Gln Arg
1               5                   10

<210> SEQ ID NO 4
<211> LENGTH: 21
<212> TYPE: PRT
<213> ORGANISM: Artificial Sequence
<220> FEATURE:
<223> OTHER INFORMATION: ubiquitin cross-linked peptide

<400> SEQUENCE: 4

Thr Leu Thr Gly Lys Thr Ile Thr Leu Glu Val Glu Pro Ser Asp Thr
1               5                   10                  15
```

Ile Glu Asn Val Lys
            20

<210> SEQ ID NO 5
<211> LENGTH: 12
<212> TYPE: PRT
<213> ORGANISM: Artificial Sequence
<220> FEATURE:
<223> OTHER INFORMATION: ubiquitin cross-linked peptide

<400> SEQUENCE: 5

Leu Ile Phe Ala Gly Lys Gln Leu Glu Asp Gly Arg
1               5                   10

<210> SEQ ID NO 6
<211> LENGTH: 6
<212> TYPE: PRT
<213> ORGANISM: Artificial Sequence
<220> FEATURE:
<223> OTHER INFORMATION: ubiquitin cross-linked peptide

<400> SEQUENCE: 6

Ala Lys Ile Gln Asp Lys
1               5

<210> SEQ ID NO 7
<211> LENGTH: 11
<212> TYPE: PRT
<213> ORGANISM: Artificial Sequence
<220> FEATURE:
<223> OTHER INFORMATION: ubiquitin cross-linked peptide

<400> SEQUENCE: 7

Met Gln Ile Phe Val Lys Thr Leu Thr Gly Lys
1               5                   10

<210> SEQ ID NO 8
<211> LENGTH: 18
<212> TYPE: PRT
<213> ORGANISM: Artificial Sequence
<220> FEATURE:
<223> OTHER INFORMATION: ubiquitin cross-linked peptide

<400> SEQUENCE: 8

Thr Ile Thr Leu Glu Val Glu Pro Ser Asp Thr Ile Glu Asn Val Lys
1               5                   10                  15

Ala Lys

<210> SEQ ID NO 9
<211> LENGTH: 15
<212> TYPE: PRT
<213> ORGANISM: Artificial Sequence
<220> FEATURE:
<223> OTHER INFORMATION: ubiquitin cross-linked peptide

<400> SEQUENCE: 9

Ala Lys Ile Gln Asp Lys Glu Gly Ile Pro Pro Asp Gln Gln Arg
1               5                   10                  15

<210> SEQ ID NO 10
<211> LENGTH: 21
<212> TYPE: PRT
<213> ORGANISM: Artificial Sequence
<220> FEATURE:
<223> OTHER INFORMATION: ubiquitin cross-linked peptide

```
<400> SEQUENCE: 10

Leu Ile Phe Ala Gly Lys Gln Leu Glu Asp Gly Arg Thr Leu Ser Asp
1               5                   10                  15

Tyr Asn Ile Gln Lys
            20

<210> SEQ ID NO 11
<211> LENGTH: 18
<212> TYPE: PRT
<213> ORGANISM: Artificial Sequence
<220> FEATURE:
<223> OTHER INFORMATION: ubiquitin cross-linked peptide

<400> SEQUENCE: 11

Thr Leu Ser Asp Tyr Asn Ile Gln Lys Glu Ser Thr Leu His Leu Val
1               5                   10                  15

Leu Arg
```

CLICKABLE CROSS-LINKER

CROSS-REFERENCE TO RELATED APPLICATION(S)

The present application claims priority to and the benefit of U.S. Provisional Application Ser. No. 61/362,652 filed on Jul. 8, 2010, the entire contents of which are incorporated herein by reference.

STATEMENT REGARDING FEDERALLY SPONSORED RESEARCH

The U.S. Government has certain rights in this invention pursuant to Grant No. CHE-0416381 awarded by the National Science Foundation.

The material in the text file entitled "13135543SEQLIST", created Oct. 17, 2011 and being approximately 2,900 bytes in size, is herein incorporated by reference in its entirety.

TECHNICAL FIELD

This application is directed to clickable cross-linkers and methods of identifying interactions using the clickable cross-linkers.

TECHNICAL BACKGROUND

The elucidation of three-dimensional structures of protein complexes and protein protein interactions (PPIs) is one of the central goals in current biological research. Proteins bind to each other to carry out specific biological functions by forming various protein complexes (Hartwell et al., *Nature* 1999, 402, C47; Pereira-Leal, et al. *Philosophical Transactions of the Royal Society B: Biological Sciences* 2006, 361, 507). On average, proteins in vivo do not act alone, but rather act as part of a protein complex comprising 10 protein subunits in the cell (Sharan et al., *Proc. Natl. Acad. Sci. U.S.A.* 2005, 102, 1974. The proteasome is a good example of a functional protein complex (King, R. W.; Deshaies, R. J.; Peters, J.-M.; Kirschner, M. W. *Science* 1996, 274, 1652). The development of new reagents and methods for identification of binding partners and their interfaces is important for advancement in proteomic science.

Chemical cross-linkers have been widely employed in analysis of three-dimensional protein structures and protein-protein interactions (PPIs) (Wong, S. S. *Chemistry of Protein Conjugation and Cross-Linking*; CRC Press, 1991; Phizicky and Fields, *Rev.* 1995, 59, 94). For identification of cross-linked proteins, traditional experimental methodologies including affinity-based chromatography and Western blot have been performed. However, no detailed structural information relative to the nature of specific protein interfaces is revealed in these experiments. Full atomistic structures of isolated proteins and their complexes can be obtained from NMR spectroscopy and X-ray crystallography but these methodologies usually require large amounts of sample for analysis. Crystallization of diffraction quality protein complexes is often the bottleneck in structure determination by X-ray crystallography.

Recently, mass spectrometry (MS)-based analysis has allowed detection of binding partners and specific contacting residues in more sensitive ways (Back et al., *J. Mol. Biol.* 2003, 331, 303; Sinz, A. *J. Mass Spectrom.* 2003, 38, 1225; Sinz, A. *Mass Spectrom. Rev.* 2006, 25, 663; Gingras et al., *Nat. Rev. Mol. Cell. Biol.* 2007, 8, 645; Lee, Y. *J. Mol. BioSyst.* 2008, 4, 816; Leitner et al., *Mol. Cell. Proteomics* 2010, 9, 1634; Petrotchenko and Borchers, *Mass Spectrom. Rev.* 2010, 29, 862; Sinz, A. *Anal. Bioanal. Chem.* 2010, 397, 3433). In vitro cross-linking and enzymatic digestion produce cross-linked peptides containing spatial information between residues reactive with the cross-linker. This topological information constrains relative distances of amino acid residues, thus aiding in the reconstruction of protein complex subunits.

For investigation of in vivo PPIs, protein complex immunoprecipitation (i.e., co-IP or "pull-down") is often performed to recover strongly interacting partners, such as an enzyme bound to its inhibitor. Co-IP requires the use of several antibodies to validate putative binding partners by running successive rounds of experiments. Alternatively, affinity tags can be infused into genes of target proteins to permit efficient purification from cell lysates (Collins and Choudhary, *Curr. Opin. Biotechnol.* 2008, 19, 324). However, many of the important signaling pathways are believed to be relayed via weak interactions that occur at the outside of strongly bound core protein complexes, and co-IP often fails to identify those weak binding partners. Chemical cross-linking is performed to freeze weak interactions by forming covalent bonds, and then sample analysis is usually combined with other targeted protein purification techniques (Tagwerker et al., *Mol. Cell. Proteomics* 2006, 5, 737; Guerrero et al., *Proc. Natl. Acad. Sci. U.S.A.* 2008, 105, 13333.

For selective and sensitive detection of cross-linked peptides, functionalized chemical cross-linking reagents are used. Various designs of cross-linking reagents have been reported, including biotinylated (Trester-Zedlitz et al.; Tang et al.; Kang et al.), isotope-coded (Chu et al.; Muller et al.; Collins et al.; Petrotchenko et al.), fluorophore labeled (Wine et al.; Sinz et al.; Sinz et al.) mass-tag labeled (Back et al.), amidinating (Lauber et al.), and chromophore labeled (Gardner et al.) cross-linking reagents. However, the addition of functional groups can often cause the cross-linker to become very bulky or less cell-permeable, and thus not very effective for in vivo cross-linking (Zhang et al.). To reduce the total size of the cross-linker, separation of the cross-linking step from conjugation of affinity tags is one effective strategy. (Trester-Zedlitz et al., *J. Am. Chem. Soc.* 2003, 125, 2416.; Tang et al., *Anal. Chem.* 2005, 77, 311; Kang et al., *Rapid Commun. Mass Spectrom.* 2009, 23, 1719; Chu et al., *J. Am. Chem. Soc.* 2006, 128, 10362; Muller et al., *Anal. Chem.* 2001, 73, 1927; Collins et al., *Bioorg. Med. Chem. Lett.* 2003, 13, 4023; Petrotchenko et al., *Mol. Cell. Proteomics* 2005, 4, 1167; Wine et al., *Anal. Chem.* 2002, 74, 1939; Sinz et al., *Biochemistry* 2001, 40, 7903; Sinz and Wang, *Anal. Biochem.* 2004, 331, 27; Back, J. W.; Hartog, A. F.; Dekker, H. L.; Muijsers, A. O.; de Koning, L. J.; de Jong, L. *J. Am. Soc. Mass Spectrom.* 2001, 12, 222; Lauber, M. A.; Reilly, J. P. *Anal. Chem.* 2010, 82, 7736; Gardner et al., *Anal. Chem.* 2008, 80, 4807; Zhang et al., *Mol. Cell. Proteomics* 2009, 8, 409.)

More recent cross-linking and enrichment strategies for separation of the cross-linking reaction from enrichment steps have recently been developed based on bio-orthogonal chemistries such as the azide-alkyne "click" cycloaddition (Rostovtsev et al.; Tornoe et al.; Baskin et al.) and Staudinger ligation (Saxon et al.) using alkyne (Chowdhury et al.; Trnka et al.) or azide (Nessen et al.; Vellucci et al.) tagged cross-linkers. Azides and alkynes are not naturally found in proteins, peptides, nucleic acids, or glycans. The orthogonality of azides and alkynes to biological processes (i.e., competing reactions) is a significant advantage of this approach. Moreover, the "click" cycloaddition can be performed under aqueous conditions, allowing the enrichment of cross-linked products by conjugation of an appropriate affinity or labeling tag. However, existing clickable cross-linkers still require screening and analysis of all cross-linked products. This analysis can require time consuming confirmation to eliminate false positives. Accordingly, an efficient and effective clickable cross-linker is desired. (Rostovtsev et al., *Angew. Chem.-Int. Edit.* 2002, 41, 2596; Tornoe et al., *J. Org. Chem.* 2002, 67, 3057; Baskin et al., *Proc. Natl. Acad. Sci. U.S.A.* 2007, 104, 16793; Saxon et al., *Science* 2000, 287, 2007; Chowdhury et al., *Anal. Chem.* 2009, 81, 5524; Trnka et al., *Mol. Cell. Proteomics* 2010, 9, 2306; Nessen et al., *J. Proteome Res.* 2009, 8, 3702; Vellucci et al., *J. Am. Soc. Mass Spectrom.* 2010, 21, 1432.)

SUMMARY

In some embodiments of the present invention, a composition including a cross-linker compound of Formula I

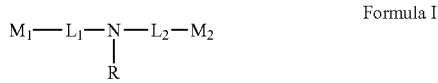

Formula I is provided, where each of $M_1$ and $M_2$ is a target conjugation group capable of conjugating to a protein, peptide or nucleic acid; each of $L_1$ and $L_2$ is independently a linkage having 1 to 20 carbon atoms or 1 to 6 polyethylene glycol groups; and R is a reporter group selected from hexynyl groups, pentynyl groups, heptynyl groups, azido-propyl groups, azido-butyl groups, or azido-pentyl groups.

In some embodiments, the composition also includes a labeling tag conjugated to the cross-linker compound, the labeling tag having a reactive group selected from hexynyl groups, pentynyl groups, heptynyl groups, azido-propyl groups, azido-butyl groups, azido-pentyl groups, cyclooctynyl groups, or difluorinated cyclooctynyl groups.

In other embodiments, a method of cross-linking at least one protein or peptide includes mixing a sample containing the at least one protein or peptide with the cross-linker compound of Formula I; conjugating a tag to the cross-linker compound in the cross-linked sample to form a tagged sample; isolating the tagged sample to form an enriched sample; ionizing the enriched sample to form an ionized sample; fragmenting the ionized sample to form fragment ions; and detecting a mass-to-charge ratio of the fragment ions.

In some embodiments of the method of cross-linking, R is selected from azido-propyl groups, azido-butyl groups and azido-pentyl groups, and the labeling tag has a reactive group selected from hexynyl groups, pentynyl groups, heptynyl groups, cyclooctynyl groups, and difluorinated cyclooctynyl groups.

In some embodiments of the method of cross-linking, R is selected from hexynyl groups, pentynyl groups, and heptynyl groups, and the labeling tag has an azide group.

In some embodiments, the method of cross-linking also includes digesting the cross-linked sample using a protease prior to conjugating a labeling tag to the cross-linker compound.

In some embodiments of the method of cross-linking, the sample containing at least one protein or peptide also includes a nucleic acid.

In some embodiments, a method of identifying intermolecular and intramolecular protein interactions in a sample includes mixing a sample containing at least one protein or peptide with the cross-linker compound of Formula I to form a cross-linked sample; conjugating a labeling tag to the cross-linker compound in the cross-linked sample to form a tagged sample; isolating the tagged sample to form an enriched sample; ionizing the enriched sample to form an ionized sample; fragmenting the ionized sample to form fragment ions; detecting a mass-to-charge ratio of the fragment ions; and based on the mass-to-charge ratio of the fragment ions, determining a peptide sequence associated with the fragment ions.

In some embodiments of the method of identifying intermolecular and intramolecular protein interactions in a sample, the sample containing at least one protein or peptide also contains a nucleic acid.

In some embodiments of the method of identifying intermolecular and intramolecular protein interactions in a sample, R is selected from azido-propyl, azido-butyl, and azido-pentyl groups, and the labeling tag has an alkyne group selected from hexynyl groups, pentynyl groups, heptynyl groups, cyclooctynyl groups, and difluorinated cyclooctynyl groups.

In some embodiments of the method of identifying intermolecular and intramolecular protein interactions in a sample, R is selected from hexynyl groups, pentynyl groups and heptynyl groups, and the labeling tag has an azide group.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is a table (Table 1) listing the mono-linked and loop-linked peptides from cross-linked ubiquitin, according to embodiments of the present invention.

FIG. 7 is a table (Table 2) listing the cross-linked peptides of ubiquitin, according to embodiments of the present invention.

FIGS. 8A, 8B, 8C, 8D, 8E, 8F, 8G, 8H, and 8I are liquid chromatography-MS (LC-MS) total ion current (TIC) chromatograms of differentially eluted ubiquitin cross-linked peptide samples, according to embodiments of the present invention.

DETAILED DESCRIPTION

Figure 1:
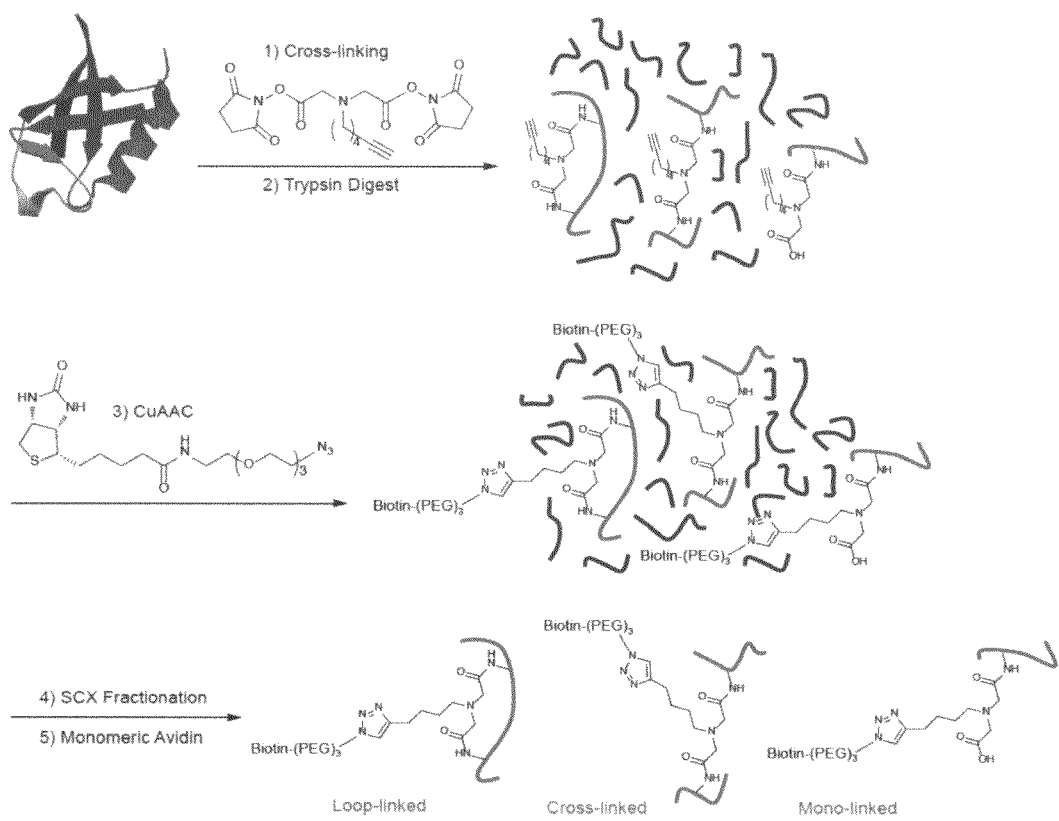
FIG. 1 is a schematic of a cross-linking reaction of a protein sample according to embodiments of the present invention.

Aspects of the present invention are directed to clickable cross-linkers (CXLs) for the investigation of three-dimensional protein structures, protein-protein interactions (PPIs), as well as protein-nucleic acid (DNA or RNA) interactions. CXLs afford distinct advantages over other currently available cross-linkers. For example, CXLs are small in size and have a cationic nature at physiological pH, giving them good water solubility and cell permeability. Also, CXLs have alkyne or azido groups for bio-orthogonal conjugation to a labeling (e.g. affinity) tag having the corresponding alkyne or azido group via a click reaction, enabling enrichment of cross-linked peptides. Further, a highly selective nucleophilic displacement reaction by the resultant 1,2,3-triazole yields a reporter ion for fast screening of cross-linked peptides. Additionally, a readily modifiable chain length between the amine-reactive groups acts as a molecular "ruler" for enhanced elucidation of structural details. Other aspects of the present invention are directed to methods of using a CXL for cross-linking proteins or peptides with their molecular binding partners (e.g. proteins, peptides, DNA, and RNA).

Cross-Linker Compound

In some embodiments of the present invention, a clickable cross-linker is represented by Formula I:

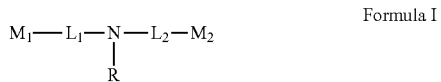

Formula I

In Formula I, each of $M_1$ and $M_2$ is a target conjugation group. As used herein, a "target conjugation group" refers to a chemical moiety that is capable of conjugating to a protein, peptide and/or a nucleic acid. Also, in some embodiments, the target conjugation group is capable of simultaneously conjugating to a protein or peptide and a nucleic acid. For example, target conjugation groups that are capable of conjugating to proteins or peptides react with a specific amino acid of the peptide or protein. Similarly, target conjugation groups that are capable of conjugating to a nucleic acid molecule (such as DNA or RNA) react with at least one specific nucleic acid base or other chemical functionality in the molecule.

In some embodiments, $M_1$ and $M_2$ are the same, thereby rendering the cross-linker compound homobifunctional. That is, when $M_1$ and $M_2$ are the same, the cross-linker makes two of the same conjugations to the peptide(s), protein(s) or nucleic acid molecules to be cross-linked. In other embodiments, $M_1$ and $M_2$ are different, i.e., the cross-linker is heterobifunctional and makes two different conjugations to the peptides(s), protein(s) or nucleic acid molecules to be cross-linked. In some embodiments, when $M_1$ and $M_2$ are different, at least one of $M_1$ and $M_2$ has a target conjugation group that is capable of conjugating to an amino acid of a protein or peptide, and the other of $M_1$ and $M_2$ has a target conjugation group capable of conjugating to a nucleic acid base, or other chemical functionality of a nucleic acid molecule. In this way, a heterobifunctional cross-linker having a target conjugation group capable of conjugating to an amino acid (e.g. an amine-reactive group) and a target conjugation group capable of conjugating to a nucleic acid base (e.g. a thymine-reactive group), can be made that is capable of specifically conjugating to both a protein or peptide and a nucleic acid molecule.

Homobifunctional and heterobifunctional target conjugation groups are well known in the art, as described, e.g., in The Molecular Probes® Handbook, 11th Edition, Cross-linking and Photoactivatable Reagents, Chapter 5, Section 5.1 *Invitrogen Life Science*; Bioconjugate Reagents, Bioconjugate Techniques, Part I and II, 2nd Edition, by Greg T. Hermanson, Published by Academic Press, Inc., 2008; and *Photoreactive Crosslinking and Labeling Reagents*, Crosslinking and Photoreactive Reagents, Chapter 5, Section 5.3, Molecular Biotechnology (MoBiTech), the entire contents of these references are herein incorporated by reference. Some non-limiting examples of $M_1$ and/or $M_2$ include: N-hydroxysuccinimide (NHS) esters (amine reactive), N-hydroxysulfosuccinimide (sulfo-NHS) esters (amine reactive), succinimidyl acetylthioacetate (SATA), carbodiimides (amine and carboxyl reactive), hydroxymethyl phosphines (amine reactive), maleimides (sulfhydryl reactive), aryl azides (primary amine reactive), fluorinated aryl azides (carbon-hydrogen (C—H) insertion), pentafluorophenyl (PFP) esters (amine reactive), imidoesters (amine reactive), isocyanates (hydroxyl reactive), psoralen (a photoreactive intercalator that reacts with thymine), vinyl sulfones (reacts with sulfhydryls, amines, and hydroxyls), pyridyl disulfides (reacts with sulfhydryls), and benzophenone derivatives (C—H bond insertion).

In some embodiments, each of $L_1$ and $L_2$ in Formula I is a linkage comprising 1 to 20 carbon atoms, or 1 to 6 polyethylene glycol groups. In some embodiments, $L_1$ and $L_2$ are the same. In other embodiments, $L_1$ and $L_2$ are different. In the cross-linker compounds according to Formula I, $L_1$ and $L_2$ and the length of the cross-linker compound are selected and/or modified according to the target protein(s), peptide(s) and/or nucleic acids to be cross-linked. As such, the chain length of the cross-linker compound of Formula I is tunable, and a set of cross-linker compounds having varying lengths may be prepared to acquire structural information. In this way, a set of cross-linker compounds having varying lengths can be used as molecular "rulers."

In some embodiments, R in Formula I is a reactive reporter group. Specifically, R reacts with a reactive group of a labeling tag for "clickable" conjugation of the tag, and participates in the nucleophilic displacement reaction (FIG. 3) resulting in a 1,2,3-triazole reporter ion that allows for facile screening of cross-linked products. In some embodiments, for example, R is selected from hexynyl groups, pentynyl groups, heptynyl groups, azido-propyl groups, azido-butyl groups, or azido-pentyl groups. In some embodiments, for conjugation to an affinity or labeling tag, when R is an alkynl group (e.g., hexynyl, pentynyl or heptynyl), the reactive group of the tag has the corresponding clickable azido group. In other embodiments, when R is an azide group (e.g., azido-propyl, azido-butyl, or azido-pentyl), the reactive group of the affinity or labeling tag has the corresponding clickable alkynyl group. In some embodiments, the clickable reaction for conjugation of the R group with a labeling tag includes copper-catalyzed azide-alkyne cycloaddition, as described in Rostovtsev et al., *Angew. Chem.-Int. Edit.* 2002, 41, 2596; Tornoe et al., *J. Org. Chem.* 2002, 67, 3057; and Baskin et al., *Proc. Natl. Acad. Sci. U.S.A.* 2007, 104, 16793, the entire contents of all of which are incorporated herein by reference. In other embodiments, the clickable reaction is copper (Cu)-free, as described in Jewett and Bertozzi, *Chem. Soc. Rev.*, 2010, 39, 1272, the entire content of which is incorporated herein by reference. Cu-free clickable chemistry catalyzes cyclooctynyl groups to corresponding azido groups.

Non-limiting examples of the alkynyl and azido reactive reporter (R) group are represented by the below formulae. The reference numbers shown with the R in the below formulae correspond to the resulting reporter ion as discussed herein.

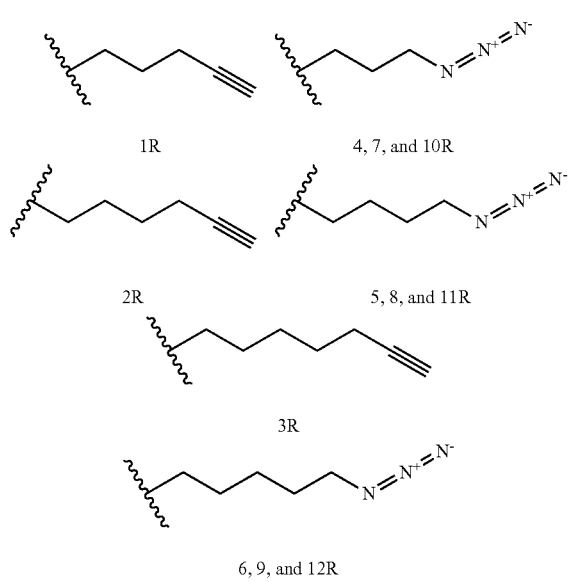

1R
4, 7, and 10R
2R
5, 8, and 11R
3R
6, 9, and 12R

Affinity or Labeling Tags of the CXLs

As discussed briefly above, the CXLs according to embodiments of the present invention can be used in conjunction with an affinity or labeling tag to aid in the identification and analysis of the cross-linked protein, peptide or nucleic acid molecules. As used herein, the terms "labeling tag," and "affinity tag" refer to chemical moieties that are conjugated to the cross-linker compound after the cross-linking reaction. These "tags" enrich the cross-linked sample by precipitation or separation of the tag species. As used throughout this disclosure and claims, the terms "labeling tag" and "tag" are used interchangeably and include non-affinity tags and affinity tags. It is known to those of ordinary skill in the art that an affinity tag is a means of labeling, and that labeling may also include non-affinity tags, for example isotope-coded tags, etc. An affinity tag is precipitated by its corresponding binding moiety. For example, biotin is precipitated by avidin; histidine is precipitated by nickel, and an antibody is precipitated by its antigen. Non-affinity labeling tags (such as, e.g., isotope-coded tags) may be selected using known methods of mass spectrometry.

By conjugating the labeling tag after the cross-linking reaction, the tag does not affect the size of the cross-linker compound and does not affect the cell permeability of the cross-linker compound. Suitable labeling and affinity tags are well known in the art. Some non-limiting examples of suitable tags include biotin (Trester-Zedlitz et al.; Tang et al.; Kang et al.) tags, isotope-coded (Chu et al.; Muller et al.; Collins et al.; Petrotchenko) tags, fluorophore labeled (Wine et al.; Sinz et al., 2001; Sinz et al., 2004) tags, mass-tag labeled (Back et al.) tags, amidinating (Lauber et al.) tags, chromophore labeled tags (Gardner et al.), and isotope-coded cleavable affinity tags (Szychowski et al.). In some embodiments, the labeling tag is selected from biotin, pegylated biotin (i.e. biotin having one or more polyethylene glycol (PEG) groups), perfluoro alkyl groups, poly-histidine, antibodies, antigens, benzophenone, sulfhydryl groups, substituted aryl azides, and unsubstituted aryl azides. In some embodiments, the labeling tag is biotin, pegylated biotin, or a perfluoroalkyl group, as described in Szychowski et al., *J. Am. Chem. Soc.* 2010, 132, 18351 and Brittain et al., *Nat. Biotechnol.* 2005, 23, 463, respectively, the entire contents of both of which references are herein incorporated by reference.

In order for the labeling tag to conjugate to (i.e. click to) the cross-linker compound, the labeling tag has a reactive group that reacts with the corresponding reactive group of the R group in Formula I above. That reaction of the tag with the R group is catalyzed by the Cu or Cu-free cycloaddition reaction, as discussed above. As such, each labeling tag includes the labeling moiety and a reactive group. Non-limiting examples of biotin-(PEG)$_3$, perfluoroalkyl, and cyclooctynl affinity tags having reactive groups are represented in the below formulae. In these formulae, the reference numbers in the cyclooctynyl structures correspond to the resulting reporter ion (which are disclosed in detail below)

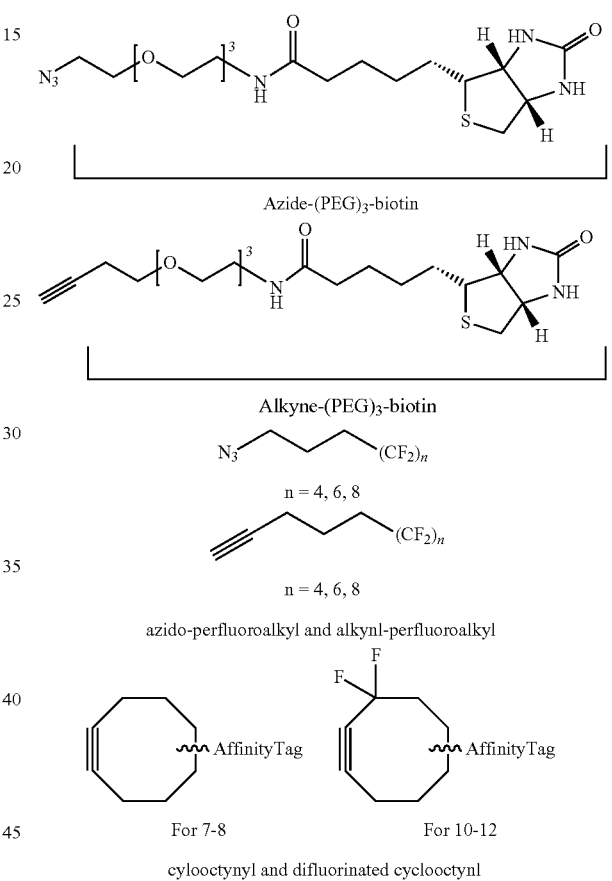

Azide-(PEG)$_3$-biotin

Alkyne-(PEG)$_3$-biotin n = 4, 6, 8 n = 4, 6, 8 azido-perfluoroalkyl and alkynl-perfluoroalkyl

For 7-8       For 10-12 cylooctynyl and difluorinated cyclooctynl

Methods of Cross-Linking

In some embodiments, a method of cross-linking a protein or peptide includes mixing a target sample having at least one protein or peptide with a cross-linker compound of Formula I either in vivo or in vitro. The in vitro sample includes at least one protein or peptide. The in vitro sample may also include a nucleic acid. In vivo, refers to a cell suspension prepared from a cell culture which inherently includes all components of the selected cell, including proteins, peptides and nucleic acids. As used herein, the phrase "the cross-linking of a protein or peptide" does not exclude the cross-linker from interacting with a nucleic acid through one of the target conjugation groups. Suitable conditions for cross-linking both in vitro and in vivo are well known to those of ordinary skill in the art.

In some embodiments, the cross-linked sample is digested with a protease to cleave the peptides or proteins in the cross-linked sample. For example, the protease used to cleave the proteins or peptides may be trypsin, Arg-C or Lys-C (Sigma Aldrich), but is not limited thereto.

In some embodiments, the digested cross-linked sample (following protease digestion if performed) is then mixed with a labeling tag having a reactive group to form a tagged cross-linked sample. As discussed above, the labeling tag may be a non-affinity or an affinity tag that conjugates to the reactive R group of the cross-linker compound. In some embodiments, the conjugation reaction of the labeling tag to the cross-linker compound is catalyzed by a copper-catalyzed azide-alkyne cycloaddition reaction or a copper-free azide alkyne cycloaddition reaction.

In order to clean up the tagged cross-linked sample after the catalyzed cycloaddition reaction, certain ligands and coupling groups can be removed from the tagged sample. For example, strong cation exchange (SCX) chromatography may be performed on the tagged sample after the cycloaddition reaction to remove, e.g., $Cu^{2+}$ ions, ligands and coupling reagents (azides or alkynes). In addition, a C18 desalting step (see, e.g., Example 4) may be performed on the SCX eluent to further remove impurities from the tagged sample.

In some embodiments, the tagged cross-linked sample may be further enriched by isolating the labeling tag. Throughout this disclosure and claims, the phrase "isolating the tagged sample" refers to precipitation, capturing, or separation of the tagged sample. For example, a biotin-$(PEG)_3$ tagged cross-linked sample may be enriched by avidin affinity chromatography. In some embodiments, affinity chromatography or label separation using a method appropriate for the label may be employed on a sample that has been prepared without SCX chromatography and/or C18 desalting. As would be understood by those of ordinary skill in the art, the complexity of the sample will determine the need to perform one or more of these additional purification steps. Also, when needed, those of ordinary skill in the art would be able to determine which purification steps to employ and how to employ them. FIG. 1 is a schematic of a cross-linking process according to one embodiment of the present invention. Specifically, in FIG. 1, the cross-linking reaction and tryptic digestion of a protein sample uses an NHS-2,2'-(hex-5-ynylazanediyl)diacetic acid cross-linker compound, and is followed by CuAAC addition of a biotin-$(PEG)_3$ affinity tag. Subsequently, SCX and avidin affinity chromatography are used to yield cross-linked, loop linked, and "dead end" mono-linked products, as shown.

In some embodiments, the enriched sample is then further separated by, e.g., liquid chromatography. Because the enriched tagged sample will include cross-linked, loop linked and mono-linked products, additional separation of these products further enriches the sample to produce the desired cross-linked product. In some embodiments, this separation step is carried out in a mass spectrometer having online liquid chromatography (LC-MS), but any other suitable method may also be used.

Figure 2:
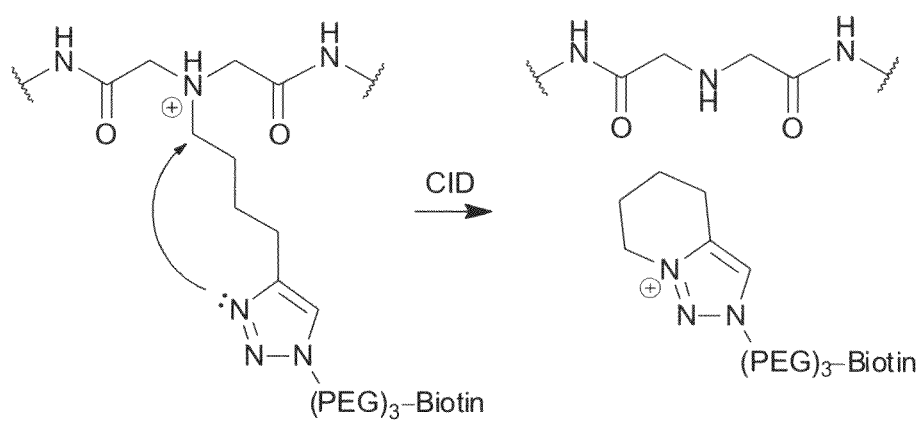
FIG. 2 is a schematic of a collision induced dissociation (CID) fragmentation reaction of a cross-linker compound according to embodiments of the present invention.

In some embodiments, the enriched tagged sample may be ionized to form an ionized sample. The ionization process may include, for example, electrospray ionization (ESI), matrix-assisted laser desorption ionization (MALDI), or fast atom bombardment (FAB). The ionized sample may subsequently be activated to fragment the ions of the ionized sample. In some embodiments, this activation (fragmentation) is carried out by collision induced dissociation (CID), electron transfer dissociation (ETD), pulsed Q dissociation (PQD), high energy C-trap dissociation (HCD) or CID-HCD. As will be apparent to those having ordinary skill in the art, tandem mass spectrometry (MS/MS) instrumentation allows for the implementation of ionization and fragmentation. A cross-linker compound represented by Formula I together with a clickable tag as disclosed herein, will yield a 1,2,3-triazole product that fragments to a predictable reporter ion having a mass-to-charge ratio that does not overlap with other species (e.g. m/z 525.3). For example, FIG. 2 shows the biotin-$(PEG)_3$ reporter ion which is released after CID of the cross-linked sample.

Pre-filtering of MS/MS scans can significantly reduce the required computational resources (especially for systems level database searching) by cutting down the number of candidate MS/MS spectra. The robust diagnostic reporter ions obtained according to embodiments of the present invention offer a technical improvement over most of the previously reported cross-linkers and affinity enrichment schemes. As such, using MS/MS, it is possible to perform scan filtering of the reporter ions to more efficiently and accurately determine the intramolecular and intermolecular (protein, peptide and/or nucleic acid) interactions associated with a cross-linked protein or peptide. Non-limiting examples of the reporter ions obtained according to embodiments of the present invention are represented by the below formulae. The reference characters in the below formulae correspond to the R group reference character and labeling tag disclosed above.

Exemplary Reporter Ions:

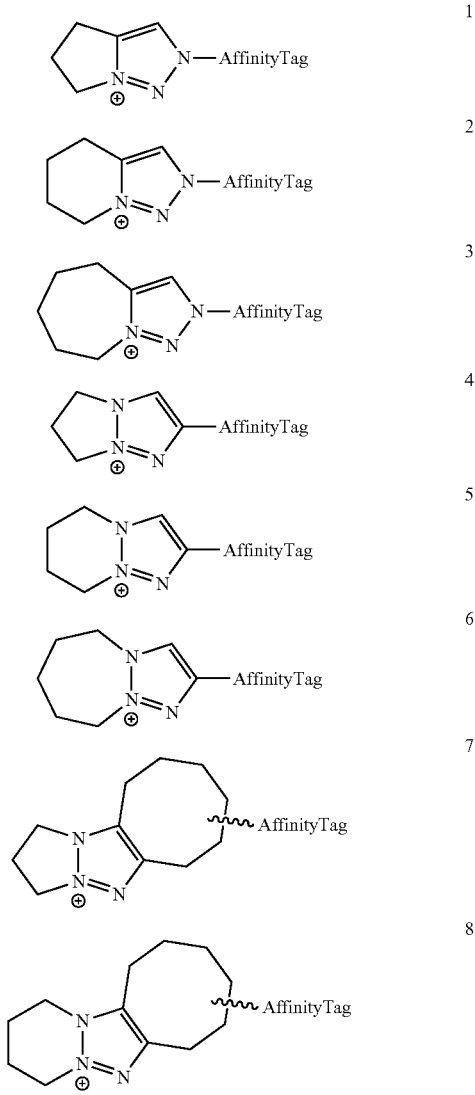

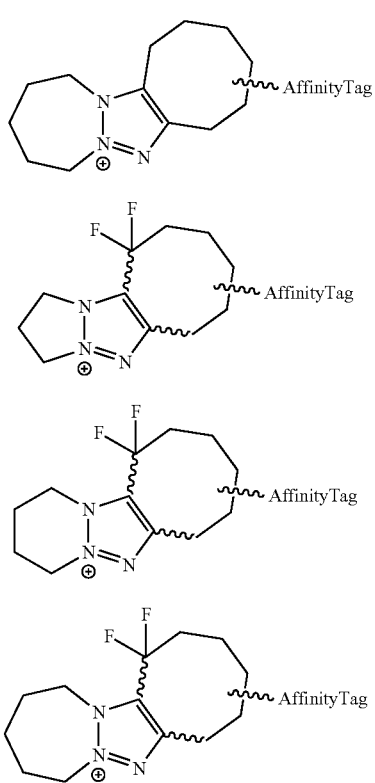

Synthesis of Cross-Linker (CXL)

Figure 3:
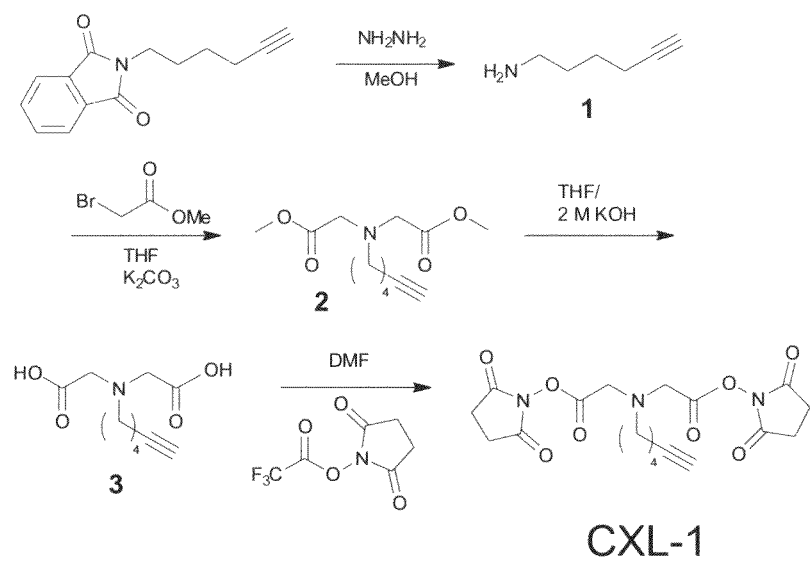
FIG. 3 is a schematic of a synthesis reaction of a cross-linker (CXL-1) according to embodiments of the present invention.

In some embodiments, synthesis of a cross-linker compound of Formula I is carried out following the general reaction scheme as shown in FIG. 3. Those having ordinary skill in the art can modify the reaction scheme based on the selection of variable groups in Formula I. That is, following the literature and the examples provided herein, the synthesis of a cross-linker compound of Formula I having a conjugated labeling tag as disclosed herein, is carried out using known methods as described in the references cited herein. For example, The Molecular Probes® Handbook, 11th Edition, Cross-linking and Photoactivatable Reagents, Chapter 5, Section 5.1 *Invitrogen Life Science*; and Bioconjugate Reagents, Bioconjugate Techniques, 2nd Edition, by Greg T. Hermanson, Published by Academic Press, Inc., 2008; Rostovtsev et al., *Angew. Chem.-Int. Edit.* 2002, 41, 2596; Tornoe et al., *J. Org. Chem.* 2002, 67, 3057; Baskin et al., *Proc. Natl. Acad. Sci. U.S.A.* 2007, 104, 16793; Jewett and Bertozzi, *Chem. Soc. Rev.*, 2010, 39, 1272, Szychowski et al., *J. Am. Chem. Soc.* 2010, 132, 18351 and Brittain et al., *Nat. Biotechnol.* 2005, 23, 463, as previously cited and incorporated herein.

The following Examples are presented for illustrative purposes only, and do not limit the scope or content of the present application.

EXAMPLES

Example 1

Synthesis of Cross-linker Compound:
NHS-2,2'-(hex-5-ynylazanediyl)diacetic acid

The general synthesis scheme is shown in FIG. 3. The reference numbers/names of the intermediates shown in the schematic are referred to and described here, e.g. (1), (2), (3), and CXL-1 are referred to in the below description of the synthesis scheme.

Synthesis of 6-Amino-hex-1-yne (1)

6-Amino-hex-1-yne was prepared from 2-(hex-5-ynyl)isoindoline-1,3-dione and hydrazine as described in the literature without modification (Nilsson et al.). The crude product was purified by flash chromatography (silica gel, dimethylene chloride:methanol=3:1 approximately 1:1) to yield 6-amino-hexyne as a pale greenish yellow oil. Yield was 30%. $^1$H NMR spectra were reproduced (Rozkiewicz et al.) ESI-MS [M+H]$^+$ m/z 98.1. (Nilsson et al., *J. Am. Chem. Soc.* 2008, 130, 11297; Rozkiewicz et al., *Angew. Chem.-Int. Edit.* 2006, 45, 5292, the entire contents of both of which are herein incorporated by reference.)

Synthesis of Dimethyl
2,2'-(hex-5-ynylazanediyl)diacetate (2)

The 6-amino-hex-1-yne (0.3 g) was added to a stirring solution of 20 mL tetrahydrafuran (THF), 2 equiv. $K_2CO_3$, and 2.4 eq methyl bromoacetate. The mixture was further stirred at room temperature for 3 h under a stream of dry $N_2$. The reaction was monitored by thin layer chromatography (TLC) using hexanes:ethyl acetate (=2:1) as the mobile phase, and the mixture was filtered after completion of the reaction. The filtrate was concentrated and purified by flash chromatography (silica gel, hexanes:ethyl acetate=1:1). The final product, dimethyl 2,2'-(hex-5-ynylazanediyl)diacetate, was concentrated by rotary evaporation and acquired as a transparent oil. Yield was 59%. ESI-MS [M+H]$^+$ m/z 242.1, $^1$H NMR (CDCl$_3$) δ 3.71 (s, 6H), 3.56 (s, 4H), 2.73 (t, 2H), 2.22 (m, 2H), 1.94 (t, 1H), 1.57 (m, 4H).

Synthesis of 2,2'-(hex-5-ynylazanediyl)diacetic acid
(3)

To the obtained approximately 1.4 g dimethyl 2,2'-(hex-5-ynylazanediyl)diacetate was added 20 mL THF and 20 mL of 2 M KOH. The mixture was stirred overnight and monitored by TLC. The organic layer was separated, and the aqueous layer was quenched by addition of 20 mL of 2 M HCl. The solvent (H$_2$O) was removed by rotary evaporation, and the resulting solid was dissolved into acetonitrile (ACN). The insoluble KCl salt was filtered, and the filtrate was concentrated by rotary evaporation. The final product of free acid was obtained as a greasy, transparent oil. Yield was quantitative. ESI-MS: [M+H]$^+$ m/z 214.1.

To obtain the hydrochloride salt, an additional 10 mL of 2 M HCl was added before removal of the solvent. Dimethyl formamide (DMF), 3×30 mL, was added to the resulting solid and filtered. The hydrochloride salt was obtained as a white solid after concentration under reduced pressure. Yield was quantitative.

Synthesis of NHS-activated
2,2'-(hex-5-ynylazanediyl)diacetic acid (CXL-1)

N-hydroxysuccinimide trifluoroacetate was prepared by stirring N-hydroxysuccinimide (NHS) and 4 eq trifluoroacetic anhydride for 5 h. The mixture was concentrated under reduced pressure and further dried under high vacuum overnight. The product was obtained as a white, highly hygroscopic solid and stored in an anhydrous desiccator before use. The obtained approximately 1.1 g 2,2'-(hex-5-ynylazanediyl)

diacetic acid was activated by 2.4 eq N-hydroxysuccinimide trifluoroacetate in 10 mL anhydrous DMF under a stream of dry $N_2$. The mixture was stirred overnight and monitored by TLC using hexanes:ethyl acetate (=2:1) as the mobile phase. After completion of the reaction, the mixture was concentrated to approximately 500 µL by rotary evaporation and subjected to flash chromatography using hexanes:ethyl acetate (=2:1) as the mobile phase. The final product, NHS-activated 2,2'-(hex-5-ynylazanediyl)diacetic acid (CXL-1) was concentrated by rotary evaporation, and obtained as a pale yellow oil. Several 200 µL aliquots of 50 mM stock solution dissolved in anhydrous dimethyl sulfoxide (DMSO) were prepared and stored at −80° C. The sealed stock aliquots were opened immediately before use, and NHS activation was verified by ESI-MS in 100% ACN. ESI-MS $[M+H]^+$ m/z 408.1, $[M+Na]^+$ m/z 420.0. This reaction yield can be improved by adding stoichiometric equivalents of triethylamine.

Example 2

Cross-Linking of Model Peptides.

A 50 µg portion of the model peptide, Ac-AA-KAAAAAAKAR (SEQ ID NO: 1) or Ac-AAAAKAAAAAR (SEQ ID NO: 2) (98% purity) was dissolved in 50 µL of HPLC-grade $H_2O$. A mixture of 5 µL CXL-1 stock solution (10 µg/µL in DMSO), 5 µL Ac-AAKAAAAAKAR (SEQ ID NO: 1) or Ac-AAAAKAAAAAR (SEQ ID NO: 2) stock solution (10 µg/µL), and 15 µL ACN was prepared. The mixture was allowed to react at room temperature for 1 h. The reaction was terminated by adding 5 µL formic acid (FA). The solvent was completely removed by speed-vac, and the residue was reconstituted in 100 µL of 0.1% FA (aq) with additional 2 µL FA to further acidify. The resulting solution was desalted using an OMIX-C18 tip (100 µL capacity) following the standard procedure. The cross-linked peptide (approximately 50 µg) was eluted in 100 µL solution of 0.1% FA, 50% ACN and 50% $H_2O$, and 5 µL of the eluted cross-linked peptide solution was diluted to 5 µM by 0.1% FA, 50% ACN, and 50% $H_2O$, and analyzed by a LCQ ion trap mass spectrometer. The remaining cross-linked peptide solution was dried for click reaction.

CuAAC with the biotin-(triethyleneglycol)-azide (biotin-$(PEG)_3$-azide) was performed as follows: 10 µg of the CXL-1 cross-linked model peptide was dissolved in 100 mM tetraethylammonium bicarbonate (TEAB) at pH 8.5, 250 µM hydrophilic ligand tris[(hydroxyethyl-triazolyl)methyl]amine (TBTA-OH), 2.5 mM $CuSO_4 \cdot 5H_2O$, 5 mM tris(2-carboxyethyl)phosphine (TCEP) hydrochloride, and 1 mM biotin-$(PEG)_3$-azide in a total volume of 100 µL containing 99% $H_2O$ and 1% DMSO (from the TBTA-OH stock). The mixture was reacted for 2 hours with gentle mixing at 37° C. and quenched by 5% FA in water (aq). The solvent was removed by speed-vac, and the residue was desalted by OMIX-C18 tip as described above. The eluent was diluted to 10 µM with 0.1% FA, 50% ACN, and 50% $H_2O$ and directly infused to the LCQ ion trap mass spectrometer for analysis.

Figure 4A:
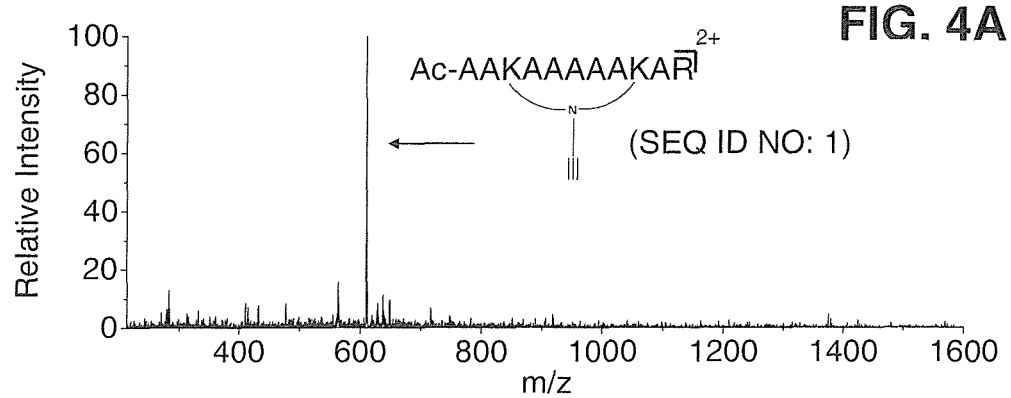
FIGS. 4A, 4B and 4C are electrospray ionization-MS (ESI-MS) and CID spectra of cross-linked peptides according to embodiments of the present invention.
Figure 4B:
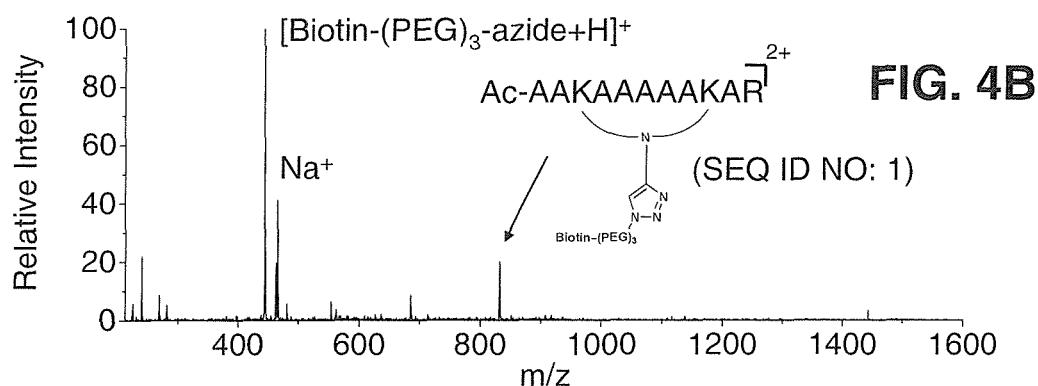
Figure 4C:
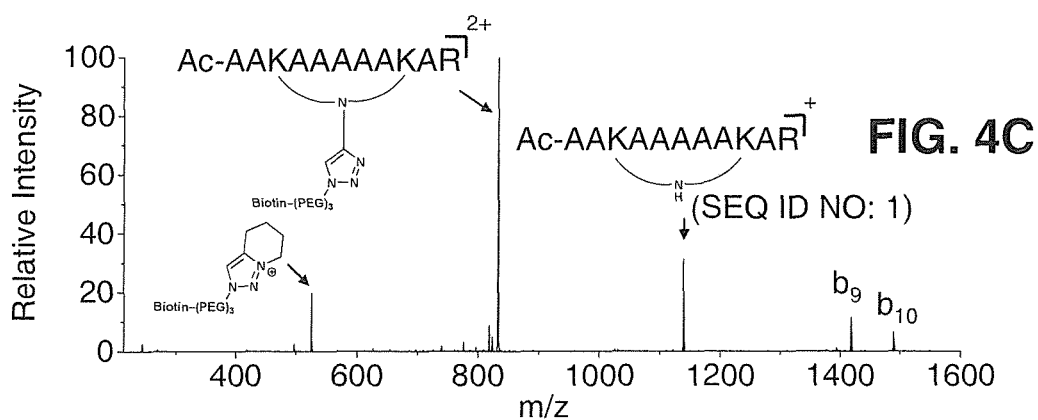

ESI-MS and CID spectra of the cross-linked model peptide, Ac-AAKAAAAAKAR (SEQ ID NO: 1), are shown in FIGS. 4A through 4C. The two lysine residues in the model peptide, Ac-AAKAAAAAKAR (SEQ ID NO: 1) are cross-linked by CXL-1 (m/z 609, FIG. 4A). Protonation sites are expected to be the arginine side chain and the central tertiary amine in the cross-linker. The 1,2,3-triazole product from conjugation of biotin-$(PEG)_3$-azide via CuAAC corresponds to the doubly charged ion at m/z 832 in FIG. 4B. No precursor ion (m/z 609) is observed, indicating quantitative conversion via CuAAC (FIG. 4B). CID of the biotin-$(PEG)_3$-azide conjugated peptide dictation yields two backbone fragments along with the reporter ion at m/z 525.3. The CID spectrum of the cross-linked and clicked Ac-AAKAAAAAKAR (SEQ ID NO: 1) peptide is shown in FIG. 4C.

Example 3

Cross-Linking of Ubiquitin

The general reaction summary of the cross-linking of ubiquitin (PDB ID: 1UBQ) according to this Example is shown in FIG. 3. Twenty micrograms of ubiquitin were dissolved in 200 µL of 1×PBS (pH=7.4), and 1.2 µL of 50 mM CXL-1 stock solution in DMSO was added and the resulting mixture was reacted for 30 min at room temperature. The reaction was quenched by 50 µL of 100 mM Tris-HCl buffer (pH=8.5) and incubated for 15 min. The cross-linked ubiquitin was concentrated to approximately 30 µL and the buffer was exchanged to 100 mM ammonium bicarbonate at pH 8.5 using Microcon YM-3K spin filter units. The trypsin digest reaction volume was adjusted by adding 185.5 µL of 100 mM ammonium bicarbonate buffer containing 2 M urea, and 2.5 µL of 100 mM $CaCl_2$. Two microliters of 0.5 µg/µL trypsin in 5 mM acetic acid (proteins:trypsin=20:1 w/w) was added and incubated for 15-18 h at 37° C. The reaction was terminated by addition of 5% FA (aq). The resulting tryptic digest was desalted by OMIX-C18 tip and a 1 µg portion was injected into a nanoLC-LTQ-FTICR mass spectrometer for analysis.

Forty micrograms of the cross-linked tryptic digest of ubiquitin were subjected to click reaction by combining resulting peptides from two identical cross-linking experiments. The desalted tryptic digest was dissolved in 100 mM TEAB, 250 µM hydrophilic ligand TBTA-OH, 2.5 mM $CuSO_4 \cdot 5H_2O$, 5 mM TCEP hydrochloride, and 1 mM biotin-$(PEG)_3$-azide in a total volume of 100 µL containing 99% $H_2O$ and 1% DMSO (from TBTA-OH stock). An additional sample was prepared by mixing 50 µg cross-linked digest of ubiquitin with 50 µg yeast cell lysate and subjected to similar click reaction conditions to demonstrate enrichment from a complex sample. Mixtures were reacted at 37° C. for 12 h with gentle shaking. Reactions were quenched by addition of 5% FA (aq).

Microspin SCX columns (200 µL scale, with 50% of the bed volume for SCX material) were used for removal of excess TBTA-OH and biotin-$(PEG)_3$-azide. A 10 µg portion of the peptides from the click reaction (25 µL) was dried by speed-vac, and the residue was reconstituted with 0.5% FA, 5% ACN (aq). Microspin SCX columns were prepared by applying 4 bed volumes (200 µL) of MeOH then $H_2O$, respectively. Activation of the SCX material was performed by 200 µL of 500 mM ammonium acetate and incubated for 1 h at room temperature. After activation, the spin columns were washed by $H_2O$ and equilibrated with 0.5% FA, 5% ACN (aq). The peptide sample solution was applied to the spin column and flushed twice to bind. The spin column was washed by 400 µL of 0.5% FA, 5% ACN (aq), which corresponds to at least 8 bed volumes of the SCX material. The peptides were fractionated by 400 µL of 50, 250, and 500 mM ammonium acetate in 0.5% FA, 25% ACN (aq), and additional 500 mM ammonium acetate solution was used for elution of highly charged cross-linked peptides. Each fraction was desalted by C18-ZipTip following manufacturer instructions, and eluents were dried by speed-vac. The residues were reconstituted with 5 µL of 0.2% FA (aq) and injected to a nanoLC-LTQ-FTICR mass spectrometer for analysis.

Monomeric avidin-biotin affinity chromatography was performed using the batch style procedure according to the manufacturer manual with modifications as described below. Peptide samples after click reaction were eluted without SCX fractionation using either 500 mM ammonium acetate in 0.5% FA, 25% ACN (aq) or 50 mM ammonium acetate in 0.1% TFA, 25% ACN (aq). The SCX eluents were dried by speed-vac and readjusted to 1×PBS at the same concentration range used in the cross-linking reaction. By incubating the mixture of the monomeric avidin resin and peptide samples at room temperature or 4° C. for 12 h under the gentle mixing, the biotin-PEG$_3$-azide conjugated peptides were bound to monomeric avidin. Unmodified peptides were washed away by flushing 4 bed volume capacity of PBS, 100 mM Tris-buffer (pH 7.4), 100 mM ammonium bicarbonate (pH 7.4), and water. The final products of interest were eluted by 0.4% TFA, 50% ACN (aq). An aliquot of the eluent was analyzed by a nanoLC-LTQ-FTICR mass spectrometer.

Figure 5A:
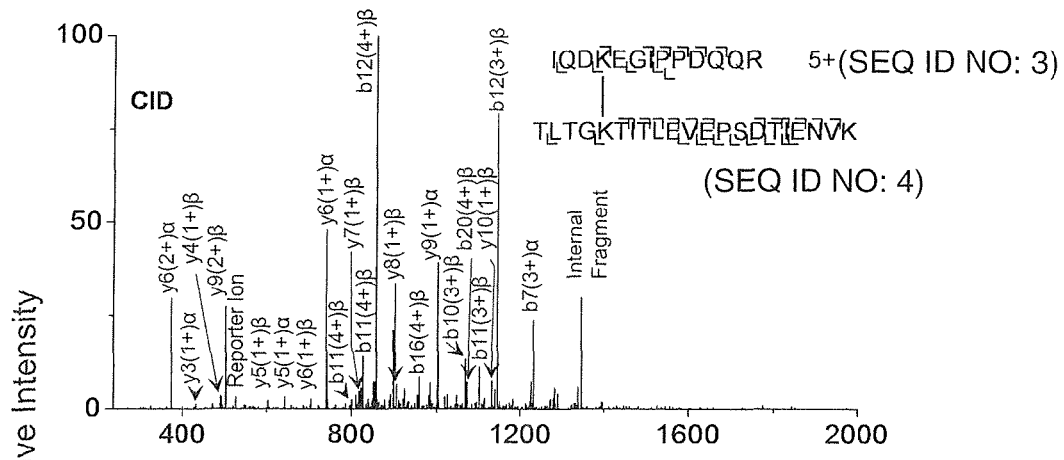
FIG. 5A is a CID spectrum of peptides cross-linked with ubiquitin, according to embodiments of the present invention.
Figure 5B:
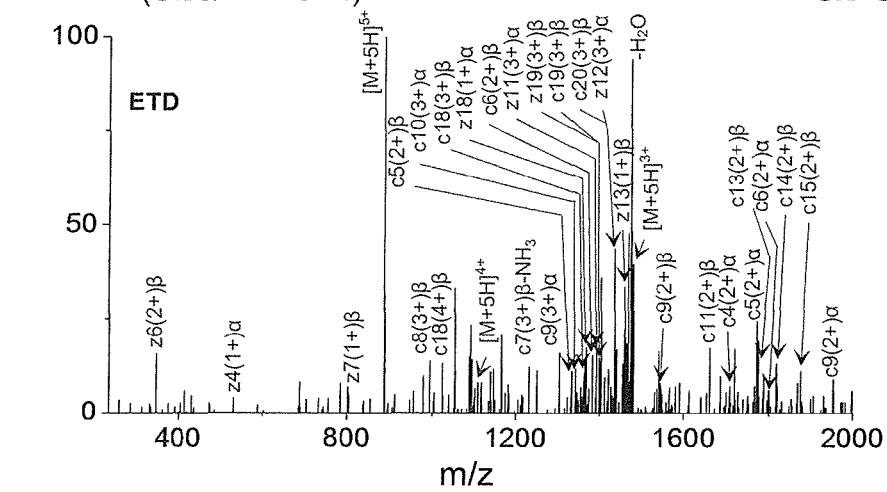
FIG. 5B is an electron transfer dissociation (ETD) spectrum of peptides cross-linked with ubiquitin, according to embodiments of the present invention.

CID and ETD of Cross-linked Peptides. Fragmentation of cross-linked peptides from ubiquitin was investigated by CID and ETD. As an example, the CID spectrum of the 5+charged $^{30}$IQD$^{33}$K^EGIPPDQQ$^{42}$R-(SEQ ID NO: 3)-$^{7}$TLTG$^{11}$K^TITLEVEPSDTIENV$^{27}$K (SEQ ID NO: 4) ion is shown in FIG. 5A. Abundant b- and y-type ions are generated and cover many sequences in each peptide chain. The diagnostic reporter ion is found at m/z 525.3 without any significant ambiguity, and it does not overlap with other backbone fragments. ETD of the 5+charged peptide ion also produces many c- and z-type ions due to its high charge state (FIG. 5B). It should be noted that the charge-reduced molecular ion species are less abundant compared to the ETD spectra of the previously reported cross-linker (Click-enabled Linker for Interacting Proteins, or CLIP) by Chowdhury et al., *Anal. Chem.* 2009, 81, 5524, the entire contents of which are herein incorporated by reference. With CLIP, the nitro group (NO$_2$) is inserted for water solubility, and neutral loss of NO$_2$ by CID can be used as a diagnostic peak. In ETD, the high electron affinity of the nitro group can initially trap a transferred electron, followed by proton transfer (Sohn et al., *J. Am. Chem. Soc.* 2009, 131, 5444.) The resulting nitronic radical stabilizes the charge-reduced species and prevents further fragmentation to form c- and z-type ions, yielding abundant charge-reduced species. With the CXLs according to embodiments of the present invention, e.g. CXL-1, there are no specific chemical bonds or residues that can generate unexpected neutral losses or stable charge-reduced species in ETD, so efficient electron based dissociation processes dominate. Generally, CuAAC with biotin-(PEG)$_3$-azide increases the charge states of peptides (Tables 1 and 2 in FIGS. 6 and 7, respectively). The tertiary amine and 1,2,3-triazole ring moderately increase the overall proton affinity for all types of cross-linked peptides. This feature apparently provides highly charged precursor ions for ETD with augmented fragmentation yields.

Example 4

Sample Clean-Up Following Click Reaction

CuAAC is a widely used bioconjugation reaction. However, seamless integration of CuAAC into the downstream proteomics workflows can be challenging due to the persistence of residual chemical reagents such as Cu$^{2+}$ ions, ligands (e.g., TBTA), and coupling reagents (azide or alkyne) (Vellucci et al., 2010). Those impurities often adversely impact the ionization efficiency of target peptides. Effective sample clean-up procedures after CuAAC are therefore very important for successful sample analysis by MS.

SCX, followed by C18 desalting is one exemplary, non-limiting clean-up procedure for the removal of non-ionic species following CuAAC. The hydrophobic TBTA reagent also has been replaced by its hydrophilic counterpart, TBTA-OH. Poor binding of TBTA-OH to the C18 matrix would result in its effective removal via the C18 desalting column. Copper ions can be removed during the same desalting step.

FIGS. 8A-8I depict LC-MS profiles of ubiquitin cross-linked peptide samples following CuAAC. The profiles of FIGS. 8A-8I depict: (FIG. 8A) a cross-linked ubiquitin digest, (FIG. 8B) a cross-linked, biotin-azide clicked ubiquitin digest after SCX clean-up without fractionation, (FIG. 8C) a cross-linked, biotin-azide clicked, avidin enriched ubiquitin digest, (FIG. 8D) a 50 mM NH4OAc SCX eluent of cross-linked, biotin-azide clicked ubiquitin digests, (FIG. 8E) a 250 mM NH4OAc SCX eluent of cross-linked, biotin-azide clicked ubiquitin digests, (FIG. 8F) a 500 mM NH4OAc SCX eluent of cross-linked, biotin-azide clicked ubiquitin digests, and (FIG. 8G) a second 500 mM NH4OAc SCX eluent of cross-linked, biotin-azide clicked ubiquitin digests, (FIG. 8H) a biotin-azide clicked 1:1 mixture of cross-linked ubiquitin and yeast cell lysate by weight after SCX clean-up without fractionation, and (FIG. 8I) an avidin enriched 1:1 mixture of cross-linked ubiquitin and yeast cell lysate.

As shown, TBTA-OH is not detected in any LC-MS profile, confirming its successful removal. Excess biotin-(PEG)$_3$-azide molecules are mostly removed by SCX clean-up due to its poor interaction with the SCX matrix, but not completely eliminated. The protonated biotin-(PEG)$_3$-azide (m/z 445.2) is eluted along with peptides (Retention Time around 55.17 min in profile (FIG. 8B) and 46.22 min in profile (FIG. 8D)), but the mass to charge ratio does not overlap with those of other cross-linked peptides, ensuring no disturbance on the sequencing. Based on its ion signal, the residual amount of biotin-(PEG)$_3$-azide after SCX clean-up seems to be less significant, and appears not to suppress peptide ionization profile (FIG. 8B). For substantially complete removal of the residual azide affinity tags, cleavable biotin tags can be employed along with streptavidin magnetic resin, which suffer less nonspecific binding (Szychowksi et al., 2010). This may allow much cleaner elution via chemical cleavage of affinity tags.

Example 5

Peptide Fractionation by SCX

Highly charged species tend to more strongly bind to the SCX matrix. Therefore, SCX can be used for sample fractionation by discriminating the charge states of analytes. Primary sample fractionation by SCX was demonstrated for sensitive detection of cross-linked peptides from abundant linear peptides by Rinner et al. *Nat. Methods* 2008, 5, 315, the entire contents of which are herein incorporated by reference. In this report, peptide fractionation of ubiquitin cross-linked peptides was performed by sequential increases in the salt concentration during the SCX elution step. Profiles in FIG. 8D, FIG. 8E, FIG. 8F and FIG. 8G show LC-MS total ion current (TIC) chromatograms of differentially eluted ubiquitin cross-linked peptide samples by applying salt gradients, i.e., 50 mM, 250 mM, 1st 500 mM, and 2nd 500 mM ammonium acetate, 0.5% FA, respectively; or direct elution using 500 mM ammonium acetate, 0.5% FA with no fractionation in profile (FIG. 8B) during the SCX elution steps. As summarized in Tables 1 and 2 (FIGS. 6 and 7, respectively), highly charged cross-linked peptides are eluted in the high concentration region. However, some of the cross-linked peptides are also co-eluted with other linear peptides at the 250 mM salt concentration (Table 2, FIG. 7 and the profile of FIG. 8E). Thus, marginal separation of cross-linked peptides is achieved by SCX fractionation. For further optimization of the separation, (an) additional elution step(s) using intermediate salt concentrations between 50 to 250 mM can be performed. Due to the low complexity of the ubiquitin cross-linked sample, SCX fractionation by itself is sufficient for separation and identification of cross-linked peptides from other linear peptides (Tables 1 and 2, FIGS. 6-7 and profiles of FIG. 8D, FIG. 8E, FIG. 8F and FIG. 8G).

Example 6

Avidin Affinity Chromatography

Monomeric avidin affinity chromatography was employed for enrichment of cross-linked peptides from the simple ubiquitin cross-linked sample prepared without SCX fractionation (FIG. 8C). Cross-linked peptides enriched by avidin affinity chromatography are summarized in Table 2 (FIG. 7). Two cross-linked peptides $^{30}$IQD$^{33}$K^EGIPPDQQ$^{42}$R-(SEQ ID NO: 3)-$^{7}$TLTG$^{11}$K^TITLEVEPSDTIENV$^{27}$K (SEQ ID NO: 4), and the homodimer of $^{43}$LIFAG$^{48}$K^QLEDG$^{54}$R ESEQ ID NO:5) that are observed in SCX fractionation are also detected by avidin affinity chromatography (Table 2), confirming the value of SCX fractionation as a separation technique. Interestingly, one additional cross-linked peptide, $^{28}$A$^{29}$K^IQD$^{33}$K-(SEQ ID NO:6) $^{30}$IQD$^{33}$K^EGIPPDQQ$^{42}$R (SEQ ID NO:3) is identified only by avidin affinity chromatography. This result demonstrates the sensitivity of affinity-based enrichment of cross-linked peptides, maximizing their detection.

For an extreme test, a highly complex peptide sample prepared by mixing equal amounts of yeast cell lysates and ubiquitin cross-linked peptides by weight, respectively, was subjected to avidin affinity chromatography. FIG. 8H and FIG. 8I depict LC-MS TIC chromatograms of the samples from SCX clean-up (FIG. 8H), and avidin enrichment (FIG. 8I) of this highly complex peptide mixture. Yeast peptides are mostly eliminated during the avidin capture step, and only a few are detected after enrichment. Other unmodified ubiquitin peptides that present no biotin tag are also mostly removed. The majority of the peaks in the LC-MS TIC chromatograms are singly charged impurities introduced after avidin affinity chromatography.[51] The two identified cross-linked peptides $^{30}$IQD$^{33}$K^EGIPPDQQ$^{42}$R-(SEQ ID NO: 3), $^{7}$TLTG$^{11}$K^TITLEVEPSDTIENV$^{27}$K (SEQ ID NO: 4), and the homodimer of $^{43}$LIFAG$^{48}$K^QLEDG$^{54}$R (SEQ ID NO: 5) reproduce those detected in the absence of yeast cell lysate (Table 2) (FIG. 7).

Example 7

Validation of Cross-linked Residues

Figure 9:
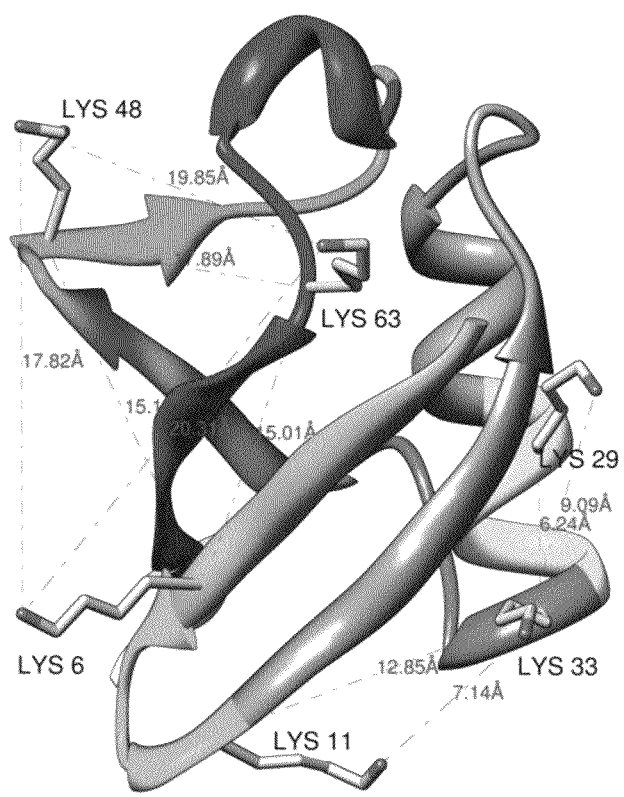
FIG. 9 is a diagram comparing cross-linked ubiquitin lysine residues to the known X-ray crystal structure, according to embodiments of the present invention.

The ubiquitin lysine residues cross-linked by CXL-1 are compared to the known X-ray crystal structure in FIG. 9 (PDB ID:1UBQ). The observed lysine pairs are all located within 20 Å. This is consistent with previous reports performed by other chemical cross-linkers that display a range of chain lengths similar to CXL-1 (Chowdhury et al., *Anal. Chem.* 2009, 81, 5524; Kruppa et al., *Rapid Commun. Mass Spectrom.* 2003, 17, 155; and Novak et al., *Eur. J. Mass Spectrom.* 2003, 9, 623, the entire contents of these references are herein incorporated by reference.) For example, in the $^{30}$IQD$^{33}$K^EGIPPDQQ$^{42}$R-(SEQ ID NO: 3), $^{7}$TLTG$^{11}$K^TITLEVEPSDTIENV$^{27}$K (SEQ ID NO: 4), cross-linked peptide, the distance between alpha carbons in each lysine residue (K11 and K33) is 12.85 Å. The maximum length of the cross-linker in the all-trans conformation is approximately 6.6 Å which is shorter by 6.25 Å. However, the distance between NZ atoms in the side chains of lysine residues is only 7.15 Å. Considering the flexibility of the lysine side chain and thermal motions in proteins, the observation of cross-linking between K11 and K33 residues is reasonable. The homodimer of the $^{43}$LIFAG$^{48}$K^QLEDG$^{54}$R (SEQ ID NO: 5) peptide is also detected as in the previous report, indicating the formation of native ubiquitin homodimers in solution.[37]

By employing chemical reactions and subsequent sample treatments, less abundant cross-linked peptides can be lost (Table 2 of FIG. 7). Compared to missing cross-linked peptides, three cross-linked peptides detected after avidin enrichment have more closely positioned lysine pairs. Therefore, the result can be rationalized by the relationship between the spatial orientation of the lysine pairs (i.e., the opportunity for cross-linking) and the resulting copy number of the cross-linked peptides, and is also consistent with the crystal structure. Therefore, no further enrichment by clicking an affinity tag is necessary for the low complexity samples (e.g., in vitro cross-linking of protein complexes that include dozens of known proteins) and SCX fractionation would still be a good choice for separation of cross-linked peptides without sacrificing sensitivity.

Example 8

Circular Dichroism Spectrometry

The CXL-1 cross-linked ubiquitin samples were analyzed by an Aviv Model 62A DS Circular Dichroism (CD) Spectrometer (Lakewood, N.J.) at room temperature. The critical instrumental parameters included: acquisition range=200 to 300 nm, step size=1.00 nm, averaging time=5 s, bandwidth=1 nm, and path length=1 mm. One scan was recorded for each spectrum. For CXL-1 cross-linked samples, 1 to 4 µL of 50 mM CXL-1 stock solution in DMSO was added to 196 to 199 µL of 0.1 mg/mL ubiquitin in 1×PBS pH 7.4 to yield a final concentration of 0.25 to 1 mM CXL-1 in 200 CD spectra were collected upon addition of CXL-1 (t=0) and after 30 min of cross-linking reaction (t=0.5 h).

Figure 10:
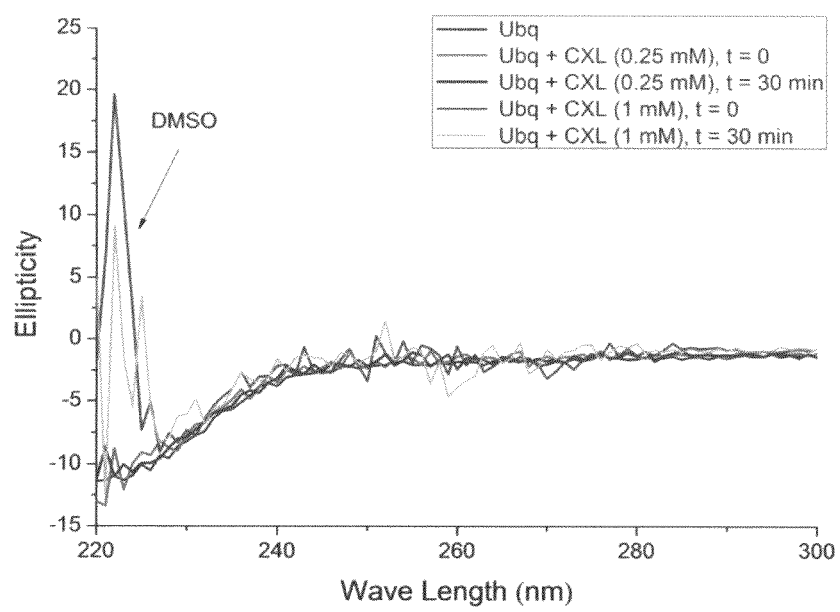
FIG. 10 is a graph of circular dichroism (CD) spectra of cross-linked ubiquitin samples, according to embodiments of the present invention.

Circular dichroism (CD) spectrometry is a useful analytical technique for quick investigation of secondary structure, folding, and binding properties of peptides and proteins (Greenfield, N. J. *Nat. Protocols* 2007, 1, 2876). Cross-linking reactions with proteins should be efficient without structural perturbation or denaturation under the working concentration of the cross-linker. To probe the structural effect, ubiquitin cross-linked by CXL-1 is examined by CD spectrometry. The CD spectra of native ubiquitin were previously recorded, yielding the secondary structure analysis of 6% α-helix, 10% β-sheet and 84% random structures, which can be observed as increasingly negative ellipticity over the range of 225 to 240 nm (Jenson et al., *Biochim. Biophys. Acta* 1980, 624, 378, the entire contents of which are herein incorporated by reference). In this work, the CD spectra were acquired in the presence of 0.25 or 1 mM CXL-1 (t=0) and after a duration of 30 min (t=30 min). The CD spectra of CXL-1 cross-linked ubiquitin samples are depicted in FIG. 10, showing no significant change in various conditions among ubiquitin samples that are native (black), cross-linked at 0.25 mM (red) or 1 mM (green) of CXL-1 and incubated for 30 min after the initiation of the cross-linking reaction (blue for 0.25 mM and pink for 1 mM CXL-1). Abundant peaks from 220 to 230 nm result from the increased DMSO portion in 1 mM CXL-1 cross-linked ubiquitin samples (from 1% to 4%). The CD signal fluctuation in 1 mM CXL-1 experiments is mainly caused by the light scattering with the increased concentrations of small molecules such as cross-linkers and DMSO. Therefore, the contribution of CXL-1 on ubiquitin secondary structure seems to be minimal or undetectable using CD spectrometry. The CD spectra show ubiquitin cross-linked at various concentrations and reaction times of CXL-1.

Example 9

In Vivo Cross-Linking of Cul1 Protein

To test the cell permeability and water solubility of CXL-1, in vivo cross-linking of HEK 293 cells, followed by Western blot analysis of the Cul1 protein were performed. The in vivo cross-linking of HEK 293 cells by CXL-1, followed by Western blot analysis was carried out as described previously with minor modifications (Lee et al., *Mol. Cell. Proteomics* 2010, Electronic preprint. doi:10.1074/mcp.M110.006460.) Briefly, to facilitate the purification of Cul1, a HEK 293-derived stable cell line capable of expressing tagged Cul1 upon tetracycline treatment was constructed using the T-REx™ (Tetracycline-regulated Expression) system (Invitrogen, Carlsbad, Calif.). The tandem tag used here consists of a hexa-histidine sequence and a biotinylation signal sequence (Tagwerker et al., 2006). Biotinylation is catalyzed by endogenous biotin ligases, which are present in all eukaryotic cells (Cronan *J. Biol. Chem.* 1990, 265, 10327). A specific lysine residue in the biotinylation signal sequence functions as an acceptor site for biotin in vivo (Kulman et al., *Protein Expr. Purif.* 2007, 52, 320).

Tagged Cul1 was induced with 1.0 μg/mL tetracycline for 4 hours in experiments for in vivo cross-linking. Twenty four hours after induction, cells were subject to in vivo cross-linking by treating 0, 0.1, 0.2, 0.5, and 1.0 mM of CXL-1, respectively, and incubated for 1 h at 37° C. After the completion of the cross-linking, cells were lysed for 30 minutes at 4° C. with the lysis buffer (0.050 M HEPES, pH 7.5, 0.0050 M Mg(OAc)2, 0.070 M KOAc, 10% glycerol, and 0.4% IGEPAL CA630). The lysate was centrifuged at 16,600 g at 4° C. for 20 min and the supernatant was used for Western blot analysis.

Figure 11:
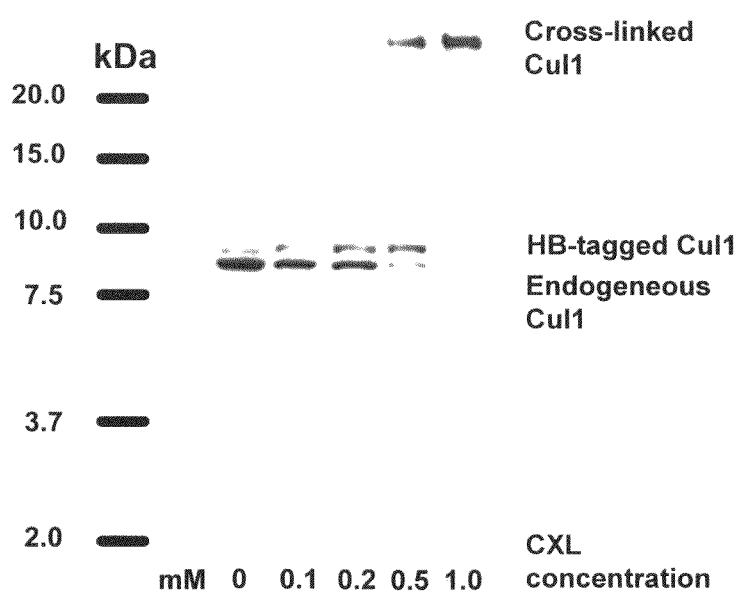
FIG. 11 is a Western blot of cross-linked Cul1 samples acquired from in vivo cross-linking of HEK 293 cells, according to embodiments of the present invention.

Cul1 is a ubiquitin ligase that attaches a ubiquitin chain on target substrates for proteasome-catalyzed degradation (Deshaies, R. J. *Annu. Rev. Cell Dev. Biol.* 1999, 15, 435). Cul1 is a prototype of the cullin ligase family, and constitutes modular ligase complexes with other binding partners. The cationic nature of CXL-1 in physiological pH and CXL-1's small size enable efficient penetration of cross-linkers into cell membranes, which is a widely employed strategy in synthesis of drug delivery carriers using cationic polymers (Nam et al., *Biomaterials* 2003, 24, 2053.) It was confirmed that CXL-1 in working concentration ranges has no or minimal cytotoxic activity on cells. It was found that treatment of CXL-1 up to 1 mM did not induce any significant cell toxicity and no visual change that may be caused by the entanglement of cell debris. Secondly, if cytoplasmic Cul1 protein is cross-linked by CXL-1, the postulated cell permeability and water solubility from the design of CXL-1 can be verified. FIG. 11 depicts the Western blot analysis of cross-linked Cul1 samples acquired from in vivo cross-linking of HEK 293 cells. From the observation of the higher molecular weight band, Cul1 is cross-linked by CXL-1 in a range of approximately 0.5 to 1.0 mM. It also indicates that CXL-1 is cell-permeable and soluble in PBS. Accordingly, CXL-1 is compatible with the cellular environment for in vivo cross-linking.

Example 10

Mass Spectrometry

The CXL-1 cross-linked Ac-AAKAAAAAKAR (SEQ ID NO: 1) and Ac-AAAAKAAAAAR (SEQ ID NO: 2) model peptides were analyzed by a LCQ-deca XP ion trap mass spectrometer (Thermo Fisher Scientific, San Jose, CA). The sample was directly infused by the standard electrospray ionization source with a constant flow at 3μL/min. The critical instrumental parameters were set up as follows: the spraying voltage at 3.0 kV, capillary voltage at 25 V, capillary temperature at 200° C., and tube lens voltage at −25 V. Fifty scans were recorded for each spectrum.

The cross-linked peptides from ubiquitin were analyzed by a nanoflow HPLC (Waters Co.) coupled on-line via a home-built nanoelectrospray ion source to a LTQ-FTICR mass spectrometer (Thermo Fisher Scientific). Samples in 5 μL of 0.2% FA (aq) were loaded onto a $C_{18}$-reversed phase column (15 cm long, 100 μm inner diameter, packed in-house with Magic $C_{18}$-AQ 5 μm resin (Michrom Bioresources) in buffer A (2% ACN, 0.2% FA) with a flow rate of 250 nl/min for 24 min and eluted with a linear gradient from 0% to 36% buffer B (98% ACN, 0.2% FA) over 110 min, followed by 10 min at 100% buffer B, at a flow rate of 250 nl/min. The column was re-equilibrated with buffer A. Mass spectra were acquired in the positive ion mode applying data-dependent acquisition with automatic switching between survey scan and tandem mass spectrum acquisition. Samples were analyzed with a top 10 method; acquiring one FTICR survey scan in the mass range of m/z 400-1600 followed by MS/MS of the ten most intense ions in the LTQ. The target ion value in the LTQ-FTICR was 500,000 for survey scan at a resolution of 50,000 at m/z 400. Fragmentation in the LTQ was performed by CID with a target value of 5,000 ions. Selected sequenced ions were dynamically excluded for 30 s. Critical mass spectrometric parameters were: spray voltage, 2.4 kV; no sheath and auxiliary gas flow; ion transfer tube temperature, 200° C.; normalized collision energy (35%) for MS/MS.

Example 11 xQuest Search

The raw files from the LTQ-FTICR mass spectrometer were converted to Mascot generic format (MGF) files using ReAdW4Mascot (version 20090305a, available from the National Institute of Standards and Technology), and all but the 150 most intense fragment ions were filtered out. The cross-linked peptide search was performed using xQuest (Rinner et al., *Nat. Methods* 2008, 5, 315). The database search parameters were as follows: 0.5 Da fragment ion mass tolerance; 0.3 Da common fragment ion mass tolerance; 10 ppm precursor ion mass tolerance; trypsin enzyme specificity (up to two missed cleavages); fixed carbamidomethyl (57.02146 Da) modification of cysteine; and variable modifications of methionine oxidation (15.99491 Da), cross-linked primary amines (177.07898 Da), mono-linked dead ends (195.08954 Da), cross-linked and biotin-(PEG)$_3$-azide clicked primary amines (621.295568 Da), mono-linked and biotin-(PEG)$_3$-azide clicked primary amines (639.305584

Da), and reporter ion (525.28537 Da). Both reporter ion-filtered and non-filtered MGF files by xQuest search were tested, but identical results were reported. Reduced MS/MS scans for xQuest search resulted in faster searching for the reporter ion-filtered MGF files.

Example 12

X-Ray Crystal Structure Analysis

Human ubiquitin (PDB ID: 1UBQ. Note: the sequences of human and bovine ubiquitin are identical) structure was analyzed by UCSF Chimera (version 1.5.3rc) (Pettersen et al., *Comput. Chem.* 2004, 25, 1605). For each pair of cross-linked lysine residue, the distances between the alpha carbons ($C_\alpha$—$C_\alpha$) and between nitrogens of ϵ-amines (NZ—NZ) were measured.

As observed from the CID and ETD spectra of cross-linked peptides originated from ubiquitin cross-linking, tandem mass spectrometric analyses can provide useful information for sequencing of cross-linked peptides and identification of protein binding partners. Especially, the reporter ion observed in the CID spectra is very useful for the reduction of the number of MS/MS spectra that are subject to the data base searching. This feature is particularly invaluable for systems level study by saving the required computational resources. The fragmentation pathway used in the formation of the reporter ion from a cross-linker compound of Formula I is actually universal when the 1,2,3-triazole ring is positioned through four methylene linkers to the tertiary amine residue regardless of the structures of the attached labeling tags. Therefore, highly selective reporter ions can be generated in a mass-tunable way by inserting various labeling tags.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A composition comprising a cross-linker compound represented by Formula I:

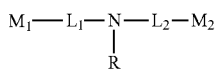

Formula I wherein:
each of $M_1$ and $M_2$ is a chemical moiety that conjugates to a functional group of a protein, a peptide, or a nucleic acid;
each of $L_1$ and $L_2$ is independently a linkage comprising 1 to 20 carbon atoms or 1 to 6 polyethylene glycol groups; and
R is a reporter group selected from the group consisting of hexynyl groups, pentynyl groups, heptynyl groups, azido-propyl groups, azido-butyl groups, and azido-pentyl groups.

2. The composition of claim 1, wherein each of $M_1$ and $M_2$ is independently selected from the group consisting of N-hydroxysuccinimide (NHS) esters, N-hydroxysulfosuccinimide (sulfo-NHS) esters, succinimidyl acetylthioacetate (SATA), carbodiimides, hydroxymethyl phosphines, maleimides, aryl azides, fluorinated aryl azides, pentafluorophenyl (PFP) esters, imidoesters, isocyanates, psoralen, vinyl sulfones, pyridyl disulfides, and benzophenone compounds.

3. The composition of claim 2, wherein each of $M_1$ and $M_2$ is an NHS ester.

4. The composition of claim 1, wherein $M_1$ and $M_2$ are the same.

5. The composition of claim 1, wherein $L_1$ and $L_2$ are the same.

6. The composition of claim 1, wherein R is a hexynyl group or an azido-butyl group.

7. The composition of claim 1, further comprising a labeling tag attached to the cross-linker compound, the labeling tag having a reactive group selected from the group consisting of hexynyl groups, pentynyl groups, heptynyl groups, azido-propyl groups, azido-butyl groups, azido-pentyl groups, cyclooctynyl groups, and difluorinated cyclooctynyl groups.

8. The composition of claim 7, wherein the labeling tag is selected from the group consisting of biotin, pegylated biotin, perfluoro alkyl groups, poly-histidines, antibodies, antigens, benzophenone, sulfhydryl groups, substituted aryl azides, unsubstituted aryl azides, isotope-coded groups, fluorophore labeled groups, mass-tag groups, amidination groups, chromophore labels, and isotope-coded cleavable affinity tags.

9. The composition of claim 8, wherein the labeling tag is selected from the group consisting of biotin, pegylated biotin, and perfluoro alkyl groups.

10. A method of cross-linking at least one protein or peptide, comprising:
mixing a sample comprising the at least one protein or peptide with the cross-linker compound of claim 1 to form a cross-linked sample;
conjugating a tag to the cross-linker compound in the cross-linked sample to form a tagged sample;
isolating the tagged sample to form an enriched sample;
ionizing the enriched sample to form an ionized sample;
fragmenting the ionized sample to form fragment ions; and
detecting a mass-to-charge ratio of the fragment ions.

11. The method of claim 10, wherein R is selected from the group consisting of azido-propyl groups, azido-butyl groups and azido-pentyl groups, and the labeling tag has a reactive group selected from the group consisting of hexynyl groups, pentynyl groups, heptynyl groups, cyclooctynyl groups, and difluorinated cyclooctynyl groups.

12. The method of claim 10, wherein R is selected from the group consisting of hexynyl groups, pentynyl groups, and heptynyl groups, and the labeling tag has an azide group.

13. The method of claim 10, further comprising digesting the cross-linked sample using a protease prior to conjugating the tag to the cross-linker compound.

14. The method of claim 13, wherein the protease is selected from trypsin, Lys-C, and Arg-C.

15. The method of claim 10, wherein each of $M_1$ and $M_2$ is independently selected from the group consisting of N-hydroxysuccinimide (NHS) esters, N-hydroxysulfosuccinimide (sulfo-NHS) esters, succinimidyl acetylthioacetate (SATA), carbodiimides, hydroxymethyl phosphines, maleimides, aryl azides, fluorinated aryl azides, pentafluorophenyl (PFP) esters, imidoesters, isocyanates, psoralen, vinyl sulfones, pyridyl disulfides, and benzophenone compounds.

16. The method of claim 15, wherein each of $M_1$ and $M_2$ is an NHS ester.

17. The method of claim 10, wherein the sample comprising the at least one protein or peptide further comprises a nucleic acid.

18. The method of claim 10, wherein $M_1$ and $M_2$ are the same.

19. The method of claim 10, wherein $L_1$ and $L_2$ are the same.

20. The method of claim 10, wherein R is a hexynyl group or an azido-butyl group.

21. The method of claim 10, wherein the tag is selected from the group consisting of biotin, pegylated biotin, perfluoro alkyl groups, poly-histidines, antibodies, antigens, benzophenone, sulfhydryl groups, substituted aryl azides, unsubstituted aryl azides, isotope-coded groups, fluorophore labeled groups, mass-tag groups, amidination groups, chromophore labels, and isotope-coded cleavable affinity tags.

22. The method of claim 21, wherein the tag is selected from biotin, pegylated biotin, and perfluoro alkyl groups.

23. The method of claim 10, wherein the isolating of the tagged sample to form an enriched sample, comprises affinity chromatography.

24. The method of claim 10, further comprising separating the enriched sample to form a separated enriched sample.

25. The method of claim 24, wherein the separating of the enriched sample comprises liquid chromatography.

26. The method of claim 10, wherein the ionizing of the enriched sample comprises matrix-assisted laser desorption ionization (MALDI), electrospray ionization (ESI), or fast atom bombardment (FAB).

27. The method of claim 10, wherein the fragmenting of the ionized sample comprises pulsed Q dissociation (PQD), electron transfer dissociation (ETD), collision induced dissociation (CID), higher energy C-trap dissociation (HCD), or CID-HCD.

28. A method of identifying intermolecular and intramolecular amino acids and/or nucleic acids in a cross-linked protein, peptide or nucleic acid sample, comprising:

mixing a sample comprising at least one protein, peptide, or nucleic acid with the cross-linker compound of claim 1 to form a cross-linked protein, peptide, or nucleic acid sample;

conjugating a labeling tag to the cross-linker compound in the cross-linked protein, peptide, or nucleic acid sample to form a tagged sample;

isolating the tagged sample to form an enriched sample;

ionizing the enriched sample to form an ionized sample;

fragmenting the ionized sample to form fragment ions;

detecting a mass-to-charge ratio of the fragment ions;

based on the mass-to-charge ratio of the fragment ions, determining an amino acid and/or nucleic acid sequence of each of the fragment ions; and based on the amino acid and/or nucleic acid sequence of each of the fragment ions, identifying the intermolecular and intramolecular amino acids and/or nucleic acids in the cross-linked protein, peptide, or nucleic acid sample.

29. The method of claim 28, further comprising digesting the cross-linked sample using a protease prior to conjugating a labeling tag to the cross-linker compound.

30. The method of claim 28, wherein the sample comprising the at least one protein or peptide further comprises a nucleic acid.

31. The method of claim 28, wherein R is selected from the group consisting of azido-propyl, azido-butyl, and azido-pentyl groups, and the labeling tag has an alkyne group selected from the group consisting of hexynyl groups, pentynyl groups, heptynyl groups, cyclooctynyl groups, and difluorinated cyclooctynyl groups.

32. The method of claim 28, wherein R is selected from the group consisting of hexynyl groups, pentynyl groups and heptynyl groups, and the labeling tag has an azide group.

33. The method of claim 28, wherein the sample is a cell suspension.

* * * * *